US005726043A

United States Patent [19]

Heim et al.

[11] Patent Number: 5,726,043

[45] Date of Patent: Mar. 10, 1998

[54] PROCESS FOR THE PRODUCTION OF PROTEASE INHIBITORS

[75] Inventors: Jutta Heim, Ramlinsburg; Peter Fürst, Basel; Thomas Hottiger, Sissach, all of Switzerland; Jochen Kuhla, Buchheim, Germany; Gabriele Pohlig, Riehen, Switzerland

[73] Assignee: Novartis Corporation, Summit, N.J.

[21] Appl. No.: 715,252

[22] Filed: Sep. 16, 1996

Related U.S. Application Data

[63] Continuation of Ser. No. 398,725, Mar. 6, 1995, abandoned, which is a continuation of Ser. No. 116,988, Aug. 30, 1993, abandoned.

[30] Foreign Application Priority Data

Sep. 4, 1992 [GB] United Kingdom ............... 92810681

[51] Int. Cl.$^6$ ............... C12P 21/06; C12N 1/15; C12N 15/81
[52] U.S. Cl. ............... 435/69.2; 435/71.2; 435/255.1; 435/320.1
[58] Field of Search ............... 435/69.2, 71.2, 435/255.1, 320.1

[56] References Cited

U.S. PATENT DOCUMENTS

| | | | |
|---|---|---|---|
| 4,940,661 | 7/1990 | Etcheverry et al. | 435/69.1 |
| 5,162,208 | 11/1992 | Lemoine et al. | 435/69.1 |

FOREIGN PATENT DOCUMENTS

| | | |
|---|---|---|
| 200655 | 5/1986 | European Pat. Off. |
| 225633 | 12/1986 | European Pat. Off. |
| 252854 | 7/1987 | European Pat. Off. |
| 340170 | 4/1989 | European Pat. Off. |
| 341215 | 5/1989 | European Pat. Off. |

OTHER PUBLICATIONS

Bailey et al, "Biochemical Engineering Fundamentals", 2nd Ed. (1986): pp. 384–384.
Henderson et al, "The Transformation of Brewing Yeasts with a Plasmid Containing the Gene for Copper Resistance" Current Genetics (1985): pp. 133–138.
Bergmeyer, M.U. (ed.), *Methods in Enzymatic Analysis*, vol. II, pp. 314–316 (1983).
Butt et al., *Microbiol. Rev.*, "Yeast metallothionein and applications in biotechnology," 51:pp. 351–364 (1987).
Butt et al., *PNAS, USA*, "Copper metallothionein of yeast, structure of the gene, and regulation of expression," 81: pp. 3332–3336 (1984).
Dohmen et al., *Curr. Genet.*, "Regulated overproduction of a-amylase by transformation of the amylolytic yeast Schwanniomyces occidentalis," *Curr. Genet.*, 15:pp. 319–325.
Etcheverry, T., *Methods Enzymol.*, "Induced expression using yeast copper metallothionein promoter," 185:pp. 319–329 (1990).

Furst et al., *Cell*, "Copper activates metallothionein gene transcription by altering the conformation of a specific DNA binding protein," 55:pp. 705–717 (1988).
Hamer et al., *Science*, "Function and autoregulation of yeast copperthionein," 228:pp. 685–690 (1985).
Hanahan, D., *J. Mol. Biol.*, "Studies on transformation of Escherichia coli with plasmids," 166:pp. 557–580 (1983).
Herskowitz and Jensen, *Methods in Enzymology*, "Putting the HO gene to work:practical uses for mating–type switching," 194:pp. 132–146 (1991).
Huibregtse et al., *PNAS USA*, "Copper–induced binding of cellular factors to yeast metallothionein upstream activation sequences," 86:pp. 65–69 (1989).
Markwardt et al., *Thromb. Haemost.*, "Pharmacological studies on the antithrombotic action of hirudin in experimental animals," 47(3):pp. 226–229 (1982).
Rudolph et al., *Gene*, "One–step gene replacement in yeast by cotransformation," 36:pp. 87–95 (1982).
Scharf et al., *FEBS Lett.*, "Primary structures of new 'iso–hirudins'", 255:pp. 105–110 (1989).
Silar et al., *Mol. Cell. Biol.*, "Heat shock transcription factor activates transcription of the yeast metallothionein gene," 11(3):pp. 1232–1238 (1991).
Sprague, G.F., *Methods in Enzymology*, "Assay of yeast mating reaction," 194:pp. 77–93 (1991).
Thiele et al., *Science*, "Mammalian metallothionein is functional in yeast," 231:pp. 854–856 (1986).
Welch et al., *EMBO J.*, "The CUP2 gene product regulates the expression of the CUP1 gene, coding for yeast metallothionein," 8:pp. 255–260 (1989).
Wright et al., *Nucleic Acids Res.*, "Chromogenic identification of oligonucleotide–directed mutants," 14:pp. 8489–8499 (1986).
Zoller and Smith, *Methods in Enzymology*, "Oligonucleotide– directed mutagenesis of DNA fragments cloned into M13 vectors," 100:pp. 468–500 (1983).
Sherman, F., *Methods in Enzymology*, "Getting Started with Yeast", 194:pp. 3–21 (1991).
Moir, D.T. et al. (1991) in Methods in Enzymology v. 194, Eds. Guthrie et al, pp. 491–507 Academic.
White way et al. (1984) Molec. Cell. Biol. Press. NY 4/(1), pp. 195–198.
Macreadie, IG et al. (1991). Gene 104,pp. 107–111.
Ordman A.B. et al. (1991), J. Steroid Biochem. Molec. Biol., 39 (4A), pp. 487–492.
Scott, J.F. et al., (1987), in Biological Research on Industrial Yeasts, Eds. Stewart et al. CRC Press Boca Raton, Fla. pp. 38–41.
Takabayashi, K. et al (1990) Yeast 6, p. 11–6A (Abstract).

*Primary Examiner*—George G. Elliott
*Assistant Examiner*—Terry A. McKelvey
*Attorney, Agent, or Firm*—Henry P. Nowak

[57] ABSTRACT

A novel process for the production of recombinant desulphatohirudin by transformed yeast strains is provided. The process makes use of an expression cassette comprising the yeast CUP1 promoter. The invention concerns also said transformed yeast strains, novel expression vectors and methods for the production thereof.

24 Claims, 4 Drawing Sheets

PROCESS FOR THE PRODUCTION OF PROTEASE INHIBITORS

This is a Continuation of Ser. No. 08/398,725, filed Mar. 6, 1995 now abandoned, which is a Continuation of Ser. No. 08/116,988, filed Aug. 30, 1993, now abandoned.

The invention pertains to the field of recombinant DNA technology and concerns a method for the production of thrombin inhibitors, more especially desulphatohirudins, with the aid of genetically engineered yeast cells, said genetically engineered yeast cells, hybrid vectors carrying the genes for said desulphatohirudins and methods for the preparation of said yeast cells and said hybrid vectors.

The hirudins are anticoagulant agents that occur naturally in leeches (e.g. in medicinal leech *Hirudo medicinalis*). The hirudins are equally acting polypeptides having an accumulation of hydrophobic amino acids at the N-terminus and of polar amino acids at the C-terminus, three disulphide bridges and the anticoagulant activity in common. A characteristic feature of most hirudins is the presence of a tyrosine sulphate residue at the C-terminal part ($Tyr^{63}$) of the molecules. Apart from the well-known hirudin variants HV1, HV2 and HV3 additional hirudins have been reported to exist in nature, see, for example, M. Scharf et al FEBS Lett. 255, 105–110 (1989), supporting the concept of hirudins as a family of isoinhibitors.

The hirudins, for example hirudin variant HV1, are the most potent and most specific known inhibitors of thrombin, the serine protease that catalyzes the final step (the conversion of the zymogen fibrinogen in clottable fibrin) in blood coagulation. Other enzymes of the blood coagulation cascade are not inhibited by hirudins. In contrast to heparin which is the preferred anticoagulant in conventional anticoagulation therapy, the hirudins exert their inhibiting action directly on thrombin and, unlike the former, do not act through antithrombin III. The only pharmacologically detectable effect of purified hirudins is the inhibition of blood coagulation and the prophylaxis of thrombosis. No side effects, such as effects on heart rate, respiration, blood pressure, thrombocyte count, fibrinogen and haemoglobin, have been observed after intravenous administration of hirudins to dogs, even in high doses. In a series of animal models hirudins have proved effective in experimental thrombosis (induced either by stasis or by the injection of thrombin), in endotoxin shock, and also in DIC (disseminated intravascular coagulation). Whenever direct comparison tests have been carried out, hirudins have proved to be superior to heparin.

In recent years cDNAs and synthetic genes coding for hirudin variants have been cloned and expressed in microbial hosts, such as *Escherichia coli* and, in particular, *Saccharomyces cerevisiae*. Although the expression products lack the sulphate monoester group at $Tyr^{63}$—and were therefore designated "desulphatohirudins"—they turned out to exhibit essentially the same biological activity as the natural sulphated hirudins. Some emphasis has been laid upon the expression of desulphatohirudin variants in the yeast *Saccharomyces cerevisiae*. Strains of *S. cerevisiae* containing episomal vectors with a desulphatohirudin expression cassette comprising a strong constitutive or inducible yeast promoter (e.g. PHO5, GAP, α-factor promoter), a yeast signal or leader sequence (e.g. the invertase or PHO5 signal sequence or the α-factor leader) and a desulphatohirudin gene provide, albeit to a differing extent, for the expression and exportation of desulphatohirudin into the culture medium from which it can be isolated (see, for example, European Patent Applications No. 200655, 225633, 252854, 340170 and 341215). The available expression systems developed for *S. cerevisiae* give minor to satisfactory yields in pharmaceutically applicable desulphatohirudin. In view of this and considering the demand for high quantities of desulphatohirudin in clinical research and, eventually, in therapy there is a need for improved methods which render possible the economic production of pharmaceutically applicable desulphatohirudins on a large scale. It is an object of the present invention to provide such methods.

Metallothioneins (MTs) are small, cysteine-rich metal binding polypeptides widely distributed among eukaryotes. *S. cerevisiae* contains a single MT protein that is encoded by the CUP1 gene. The CUP1 locus has been shown to confer copper resistance to yeast cells. Two natural variants of *S. cerevisiae* with respect to copper resistance are known: Strains sensitive to 0.3 mM copper contain a single copy of the CUP1 locus (consisting of two tandemly arranged copies of the CUP1 gene) and are designated $cup1^s$, while strains resistant to 0.3 mM copper contain several tandemly repeated copies of the CUP1 locus and are designated $CUP1^r$. Copper resistance relies on a combination of CUP1 amplification and CUP1 translational induction following the addition of exogenous copper. A cis-acting upstream activation site ($UAS_c$) required for promotion of copper-inducible transcription of the CUP1 gene has been identified as well as the binding of a cellular factor to $UAS_c$. The binding factor is the product of the ACE1 (=CUP2) gene which is essential for the copper-induced transcription of the CUP1 gene. The ACE1 protein is a transcriptional activator that binds copper ions thereby altering its conformation and activating its DNA-binding domain. The conformational change of the ACE1 protein eventually allows the CUP1 gene to be transcribed. An important feature of the CUP1 system is its autoregulation. This depends on the ability of the CUP1 protein to bind itself copper ions. Thus, the CUP1 protein appears to repress its own synthesis by complexing free copper ions in the cells, which, in turn, interferes with ACE1 activation.

There are few examples in literature of the use of the inducible CUP1 promoter for the expression of heterologous proteins by yeast (cf. T. R. Butt et al., Microbiol. Rev. 51, 351–364, 1987; T. Etcheverry, Methods Enzymol. 185, 319–329, 1990; U.S. Pat. No. 4,940,661). The methods described include culturing a transformed yeast strain harboring an expression vector with a CUP1 expression cassette in yeast minimal media containing copper ions. Chemically defined minimal media are chosen because it is generally believed that components (proteins etc.) of complex media will interact with (complex) the copper ions thus preventing ACE1 activation. The attainable cell density (OD value) and, as a consequence, the titers obtainable are correspondingly low. The latter results have so far limited the widespread application of the CUP1 promoter system in biotechnological research and production.

Surprisingly, it has now been found that, contrary to all expectations, complex yeast media can be used in connection with the copper induced CUP1 expression cassette without any deleterious effect on expression level or efficiency being observable. Furthermore, when the CUP1 promoter is used in a pseudo-constitutive manner, i.e. the culture medium is supplied with copper right at the time of inoculation, to direct the secretion of desulphatohirudin by yeast into the culture medium it is surprisingly found that this promoter is superior to strong constitutive yeast promoters, such as the shortened (constitutive) GAP ("GAPFL") promoter, although the heterologous protein desulphatohirudin is non-toxic to the yeast cells.

Accordingly, the present invention relates to an improved method for the production of desulphatohirudin comprising culturing in a complex culture medium a yeast strain harboring a yeast expression vector comprising a desulphatohirudin expression cassette consisting of the yeast CUP1 promoter operably linked to a first DNA sequence encoding a yeast signal peptide linked in the proper reading frame to a second DNA sequence coding for desulphatohirudin, and a DNA sequence containing yeast transcription termination signals, and isolating the produced desulphatohirudin from the culture broth, wherein the culture medium is supplied, right at the time of inoculation, with a CUP1 promoter inducing amount of a copper salt.

The term "desulphatohirudin" is intended to embrace all desulphatohirudin compounds described in literature or obtainable from a transformed microorganism strain containing DNA which codes for a desulphatohirudin. Such desulphatohirudins are, for example, desulphatohirudin variants HV1, HV2 and HV3 (PA), as well as other hirudin proteins described by M. Scharf et al. (supra). It is to be understood that hirudin derivatives having hirudin activity (i.e. having a thrombin inhibiting action) are also covered by the term "desulphatohirudin". Such derivatives are, for example, C-terminally shortened desulphatohirudins, i.e. desulphatohirudins lacking one to seven, preferably one to four, amino acids at the C-terminus, and muteins of hirudins differing from the latter by the substitution of single or plural, e.g. one to five, amino acids for the genuine amino acids. The preferred desulphatohirudin is desulphatohirudin variant HV1.

Suitable yeast strains according to the invention include strains of *Saccharomyces cerevisiae* containing the endogenous two-micron plasmid or such strains which have been cured of said endogenous two-micron plasmid (see European Patent Application No. 340170). The preferred yeast strains according to the invention are devoid of the endogenous two-micron plasmid (so-called "cir$^0$ strains"). Preferred yeast strains are single or multiple protease-deficient yeast strains, i.e. yeast strains lacking especially carboxypeptidase yscα and yscY proteolytic activity and, optionally additionally, protease yscA and/or yscB activity (see European Patent Application No. 341215). The yeast strains suitable for the process according to the present invention contain 0–16, in particular 2–6, copies of the chromosomal CUP1 gene. Optionally, the yeast strains according to the invention contain 1–3 additional copies of the chromosomal ACE1 gene. In a further embodiment of the present invention, yeast strains having a mutation in the endogenous heat shock factor protein are used. Such mutants lead to enhanced CUP1 transcription levels under condition of stress (cf. P. Silar et al., Mol. Cell. Biol. (1991) 11, 1232–1238).

The yeast strains, e.g., from the genus *S. cerevisiae*, may be haploid, diploid or polyploid. Preferred yeast strains have a ploidity equal or greater than two, these strains are, e.g., octaploid, tetraploid, triploid and especially diploid. A diploid or polyploid strain of *S. cerevisiae* is constructed, e.g., by mating two haploid strains of mating types a and α or by protoplast fusion. In a preferred embodiment of the invention, the diploid yeast strains are formed using to haploid and isogenic yeast strains that only differ in the mating type.

The transformed yeast strains are cultured using methods known in the art. Thus, the transformed yeast strains according to the invention are cultured in a liquid complex culture medium containing components which are essential for the yeast strain to survive and to grow, such as assimilable sources of carbon and nitrogen, inorganic salts, vitamins, growth promoting substances such as additional amino acids, sugars and the like.

Corresponding complex culture media which can be used for culturing yeast are known in the art. For examples, such culture media contain tryprone, peptone, meat extracts, malt extracts, yeast extracts, casamino acids, corn steep liquor, soy bean flour etc., and especially mixtures thereof and are optionally additionally supplemented with sugars (e.g. dextrose, glucose, sucrose etc.), vitamins (e.g. biotin), individual amino acids, inorganic salts (for example, sulphates, chlorides, phosphates and carbonates of sodium, potassium, magnesium and calcium, furthermore corresponding salts of trace elements, such as iron, zinc and manganese) and the like taking into account that all essential components as outlined above are to be present in the medium. A preferred culture medium is the commercially available medium YPD (yeast extract, peptone, dextrose; cf. Methods Enzymol. 194, 13) optionally supplemented with inorganic salts and vitamins.

The cultivation is carried out by employing conventional techniques. The culturing conditions, such as temperature, pH of the medium and fermentation time are selected in such a way that maximal levels of desulphatohirudin are produced. A chosen yeast strain is preferably grown under aerobic conditions in submerged culture with shaking or stirring at a temperature of about 25° to 33° C., preferably at about 28° C., at a pH value of from 4 to 7, for example at approximately pH 5 to 6, and for at least 1 to 3 days, preferably 3 to 4 days, such that satisfactory yields of desulphatohirudin are obtained. Culturing can be carried out either as a batch process, as a fed batch process, as a repeated fed batch process, or continuously.

Right at the time of inoculation, the culture medium is supplied with a CUP1 promoter inducing amount of a copper(II) salt, particularly copper sulphate. The optimum amount of copper (the amount which provides for the maximal titers in desulphatohirudin) depends, above all, on the genetic background of the host cell, the components of the expression vector used and the composition of the culture medium, and can be determined by the artisan applying routine tests, e.g. by "titration" (determining the desulphatohirudin titer by HPLC as a function of the amount of copper added). A routine test has been described by T. Etcheverry (loc. cit., page 324 therein). The determination of the right copper concentration is important because unnecessarily high copper levels may cause an inhibition of the metabolic machinery of the cell.

Irrespective of the yeast strain, promoter and signal peptide used, the produced desulphatohirudin is predominantly (i.e. more than 90%) secreted into the culture medium. The desulphatohirudin can be isolated therefrom by conventional means. For example, the first step consists usually in separating the cells from the culture fluid by means of centrifugation. The resulting supernatant can be enriched for desulphatohirudin by treatment with polyethyleneimine so as to remove most of the non-proteinaceous material, and precipitation of the proteins by saturating the solution with ammonium sulphate. Host proteins, if present, can also be precipitated by means of acidification with acetic acid (for example 0.1%, pH 4–5). A further enrichment of desulphatohirudin can be achieved by extracting the acetic acid supernatant with n-butanol. Other purification steps include, for example, desalination, chromatographic processes, such as ion exchange chromatography, gel filtration chromatography, partition chromatography, HPLC, reversed phase HPLC and the like. The separation of the constituents of the mixture is also effected by dialysis, according to charge by means of gel electrophoresis or carrier-free electrophoresis, according to molecular size by means of a suitable Sephadex column, by affinity chromatography, for example with antibodies, especially monoclonal antibodies, or with thrombin coupled to a suitable carrier for affinity chromatography, or by other processes, especially those known from the literature. In general, only a few purification steps are required in order to get a desulphatohirudin product which is essentially free of contaminants.

The test with anti-hirudin or anti-desulphatohirudin antibodies (for example monoclonal antibodies), the thrombin test [M. U. Bergmeyer (ed.), Methods in Enzymatic Analysis, Vol. II, p. 314–316, Verlag Chemie, Weinheim (FRG) 1983] or the blood coagulation test [F. Markwardt et al., Thromb. Haemost. 47, 226 (1982)] can be used to detect the hirudin activity during the isolation and purification steps. It is also possible to use chromatographical means, such as HPLC.

The transformed yeast cells according to the invention can be prepared by recombinant DNA techniques comprising the steps of providing a yeast expression vector comprising a desulphatohirudin expression cassette consisting of the yeast CUP1 promoter operably linked to a first DNA sequence encoding a yeast signal peptide linked in the proper reading frame to a second DNA sequence coding for desulphatohirudin, and a DNA sequence containing yeast transcription termination signals, transforming a yeast strain with said yeast expression vector, and selecting transformed yeast cells from untransformed yeast cells.

Yeast expression vectors

The invention concerns a yeast expression vector comprising a desulphatohirudin expression cassette consisting of the yeast CUP1 promoter operably linked to a first DNA sequence encoding a yeast signal peptide linked in the proper reading frame to a second DNA sequence coding for desulphatohirudin, and a DNA sequence containing yeast transcription termination signals.

The DNA sequence of the CUP1 promoter is known (T. R. Butt et al., Proc. Natl. Acad. Sc. U.S.A. 81 (1984) 3332–3336). Accordingly, the CUP1 promoter can be provided by chemical DNA synthesis or isolated from genomic S. cerevisiae DNA using suitable DNA probes, e.g. by polymerase chain reaction (PCR). The CUP1 promoter used in the present invention includes the transcription initiation signals and the upstream activation sequence (UAS$_c$) located at positions –105 to –148 (relative to the transcription start site of CUP1; P. Fürst et al. Cell 55 (1988) 705–717). Preferably, use is made of existing restriction sites 5' of UAS, e.g. of the BamHI site located at position –455 of the CUP1 gene (T. R. Butt et al., supra) and of a restriction site 3' of the transcription start signals (e.g. a EcoRI site) artificially introduced by chemical synthesis or by the oligonucleotide used in PCR. The resulting restriction fragment, e.g. a 0.4 Kb BamHI-EcoRI fragment, especially that contained in the construct depicted in SEQ ID NO:1, can be linked to the DNA sequence encoding a yeast signal peptide. The protein encoded by the nucleic acid set forth as SEQ ID NO:1 is set forth as SEQ ID NO:2.

The DNA sequence encoding a yeast signal peptide ("signal sequence") is preferably derived from a yeast gene coding for a polypeptide which is ordinarily secreted. Yeast signal sequences are, for example, the signal and prepro sequences of the yeast invertase, α-factor, pheromone peptidase (KEX1), "killer toxin" and repressible acid phosphatase (PHO5) genes and the glucoamylase signal sequence from Aspergillus awamori. Additional sequences, such as pro- or spacer-sequences which may carry specific processing signals can also be included in the constructions to facilitate accurate processing of precursor molecules. For example, the processing signals contain a Lys-Arg residue, which is recognized by a yeast endopeptidase located in the Golgi membranes. The preferred signal sequences according to the present invention are those of the yeast PHO5 gene and of the yeast invertase gene.

The DNA sequence coding for desulphatohirudin or derivative thereof can be isolated from genomic leech DNA or a double-stranded desulphatohirudin DNA (desulphatohirudin ds cDNA) is produced complementary to desulphatohirudin mRNA, or a gene coding for the amino acid sequence of desulphatohirudin or derivative thereof is produced by means of chemical and enzymatic processes, in a manner known per se.

A DNA sequence containing yeast transcription termination signals is preferably the 3' flanking sequence of a yeast gene which contains proper signals for transcription termination and polyadenylation. The preferred flanking sequence is that of the yeast PHO5 gene.

The yeast CUP1 promoter, the DNA sequence coding for the signal peptide, the DNA sequence coding for desulphatohirudin and the DNA sequence containing yeast transcription termination signals are operably linked to each other, i.e. they are juxtaposed in such a manner that their normal functions are maintained. The array is such that the CUP1 promoter effects proper expression of the signal sequence-desulphatohirudin gene complex, the transcription termination signals effect proper termination of transcription and polyadenylation and the signal sequence is linked in the proper reading frame to the desulphatohirudin gene in such a manner that the last codon of the signal sequence is directly linked to the first codon of the gene for desulphatohirudin and secretion of mature desulphatohirudin occurs. The CUP1 promoter is preferably joined to the signal sequence between the major mRNA start and the ATG of the CUP1 gene. The signal sequence has its own ATG for translation initiation. The junction of these sequences may, for example, be effected by means of synthetic oligodeoxynucleotide linkers carrying the recognition sequence of an endonuclease.

Apart from the desulphatohirudin expression cassette, the expression vectors according to the invention comprise a yeast replication origin. Accordingly, the vectors comprise a DNA segment originating from two-micron DNA containing the origin of replication or, if a two-micron DNA free strain of yeast is used, total two-micron DNA. The latter type of vectors is preferred. For example, the vectors according to the invention contain the complete two-micron DNA in an uninterrupted form, i.e. two-micron DNA is cleaved once with a restriction endonuclease, the linearised DNA is linked with the other components of the vector prior to recircularization. The restriction site is chosen such that normal function of the REP1, REP2 and FLP genes and of the ORI, STB, IR1 and IR2 sites of two-micron DNA is maintained. Optionally, the restriction site is chosen such that the D gene of two-micron DNA too is kept intact. Suitable restriction sites are, for example, the unique PstI site located within the D gene and the unique HpaI and SnaBI sites located outside of all of said genes and sites. However, it is likewise possible to insert the expression cassette and further components (cf. below) at different (such as two) restriction sites, especially those mentioned above, within two-micron DNA.

Preferably, the expression vectors according to the invention include one or more, especially one or two, selective genetic markers for yeast and such a marker and an origin of replication for a bacterial host, especially *Escherichia coli*.

In a preferred embodiment of invention, the two regions between invertedly repeated FRT sites of the circular form of the two-micron DNA have approximately the same length.

Such a plasmid derivative may comprise only two invertedly repeated FRT sites or an additional, third FRT site. The former kind of plasmid is hereinafter called a "symmetric two micron-like hybrid vector". The latter kind of plasmid is hereinafter called "symmetric two micron-like disintegration vector" despite it is not a real symmetric plasmid but gives rise to a symmetric two micron-like hybrid vector in the yeast cell transformed therewith.

A symmetric two micron-like hybrid vector of the invention does preferentially not contain bacterial or viral DNA sequences, i.e. DNA derived from a bacterial genome, plasmid or virus. However, a two micron-like disintegration vector of the invention may comprise DNA sequences of prokaryotic origin between the two directly repeated FRT sites which are excised from the vector in the transformed yeast cell in which the symmetric two micron-like hybrid vector is generated from the disintegration vector. These DNA sequences are bacterial sequences as described below and can provide to the vector essential structural or functional features or can also only have the function of filling up the two regions between the two invertedly repeated FRT sites of an unsymmetric two micron-like plasmid derivative or of an "unsymmetric" disintegration vector in order to construct a symmetric two micron-like hybrid vector or a symmetric disintegration vector.

In a two micron-like hybrid vector which is symmetric within the meaning of the present invention or in a disintegration vector which gives rise to such a symmetric two micron-like hybrid vector the lengths of the regions located between the two invertedly repeated FRT sites have a ratio from about 1:1 up to about 5:4, i.e. the larger region is up to about 20% larger than the smaller one.

As to the selective gene markers for yeast, any marker gene can be used which facilitates the selection for transformants due to the phenotypic expression of the marker gene. Suitable markers for yeast are, for example, those expressing antibiotic resistance or, in the case of auxotrophic yeast mutants, genes which complement host lesions. Corresponding genes confer, for example, resistance to the antibiotics G418, hygromycin or bleomycin or provide for prototrophy in an auxotrophic yeast mutant, for example the URA3, LEU2, LYS2 or TRP1 gene.

As the amplification of the expression vectors is conveniently done in a prokaryote, such as *E. coli*, a prokaryote, e.g. *E. coli*, genetic marker and a prokaryote, e.g. *E. coli*, replication origin are included advantageously. These can be obtained from corresponding prokaryotic plasmids, for example *E. coli* plasmids, such as pBR322 or a pUC plasmid, for example pUC18 or pUC19, which contain both prokaryotic, e.g. *E. coli*, replication origin and genetic marker conferring resistance to antibiotics, such as ampicillin.

Apart from the CUP1-desulphatohirudin expression cassette, replication origin(s) and genetic marker(s) the expression vectors according to the invention contain optionally additional expression cassettes, such as 1 to 3 additional desulphatohirudin expression cassettes and/or one additional transcriptional activator ACE1 expression cassette. The additional desulphatohirudin expression cassette (s) are identical to or different from each other and are identical to or different from the CUP1-desulphatohirudin expression cassette already present on the vector and each comprise a yeast promoter operably linked to a first DNA sequence encoding a signal peptide linked in the proper reading frame to a second DNA sequence encoding desulphatohirudin and a DNA sequence containing yeast transcription termination signals. A suitable yeast promoter in such an additional desulphatohirudin expression cassette is, for example, any constitutive or inducible yeast promoter which can be used for the expression of desulphatohirudin by yeast in complex media. Such promoters are e.g. the CUP1, GAPDH (including shortened constitutive versions thereof, e.g. GAPFL etc.) GAL1(10), PYK, TPI, ADH and PGK promoters. Preferred is the constitutive GAPFL promoter. Suitable signal sequences and transcription termination signals are especially those described above. Corresponding desulphatohirudin expression cassettes are, for example, described in European Patent Application No. 341215. An additional ACE1 expression cassette includes its own transcriptional and translational initiation and termination signals or, in the alternative, is transcriptionally controlled by a constitutive or inducible yeast promoter different from the ACE1 promoter, such as the CUP1 or a constitutive (shortened) GAPDH promoter (e.g. GAPFL promoter). A suitable ACE1 expression cassette is, for example, contained in the *S. cerevisiae* genomic 1.7 kb EcoRV fragment (cf. P. Fürst et al (1988) Cell 55, 705–717). The genuine ACE1 promoter therein can be replaced by another yeast promoter, e.g. the CUP1 promoter, by conventional means and methods. The direction of transcription of the additional desulphatohirudin and/or ACE expression cassettes is not crucial and may be the same as or opposite to the direction of transcription of the CUP1-desulphatohirudin expression cassette already present in the vectors of the invention.

The invention concerns also a method for the preparation of the novel expression vectors as defined above. The expression vectors according to the invention are prepared by methods known in the art, for example by linking the CUP1-desulphatohirudin expression cassette consisting of the yeast CUP1 promoter operably linked to a first DNA sequence encoding a yeast signal peptide linked in the proper reading frame to a second DNA sequence coding for desulphatohirudin, and a DNA sequence containing yeast transcription termination signals, the DNA fragments containing selective genetic markers for yeast and for a bacterial host, the origins of replication for yeast and for a bacterial host, and the optionally additional desulphatohirudin and/or ACE1 expression cassettes in the predetermined order using conventional chemical or biological in vitro synthesis procedures. Preferentially the vectors are constructed and prepared using recombinant DNA techniques. For the preparation by recombinant DNA techniques suitable DNA fragments are ligated in vitro in conventional manner. The ligation mixture is then transformed into a suitable prokaryotic or eukaryotic host depending on the nature of the regulatory elements used, and a transformant containing the desired vector is selected according to conventional procedures. The vectors can be multiplicated by means of the transformed hosts and can be isolated in conventional manner. The choice of the host depends on the regulatory sequences located on the vector. As the expression vectors of the invention preferentially comprise regulatory sequences functional in prokaryotes, e.g. *E. coli*, a prokaryotic host, e.g. *E. coli*, is preferred for the construction and multiplication of the vector.

Transformed yeast strains

The invention concerns furthermore a yeast strain harboring a yeast expression vector comprising a desulphatohirudin expression cassette consisting of the yeast CUP1 promoter operably linked to a first DNA sequence encoding a yeast signal peptide linked in the proper reading frame to a second DNA sequence coding for desulphatohirudin, and a DNA sequence containing yeast transcription termination signals, and a method for the production thereof.

The transformation of yeast with the expression vectors according to the invention may be accomplished according to methods known in the art.

Preferred yeast strains are those mentioned above, especially strains of *S. cerevisiae* which have been cured of the endogenous two-micron plasmid ("cir$^0$ strains") and are singly or multiply deficient in yeast proteases, such as carboxypeptidases yscα and yscY. Methods for the production of such yeast strains are described, for example, in European Patent Applications Nos. 340170 and 341215. Yeast strains containing 0–16, in particular 2–6, copies of the chromosomal CUP1 gene are known or can be prepared in a manner known per se. For example, starting with a conventional copper sensitive yeast strain containing e.g. 2–4 chromosomal copies of the CUP1 gene there can be made yeast strains having less copies of the CUP1 gene by introducing deficiencies into the yeast genome, e.g. by site-directed mutagenesis or gene-disruption or gene replacement [cf. H. Rudolph et al., Gene, 36 (1985) 87–95]. As the sequence of the chromosomal CUP1 gene is known the latter can be made defective by insertion, substitution or deletion making use of the well-known site directed mutagenesis procedure [see, for example, M. J. Zoller and M. Smith (1983) Methods Enzymol. 100, 468] which involves the preparation of an appropriately devised mutagenic oligodeoxyribonucleotide primer. Alternatively, the genomic CUP1 gene can be replaced by foreign DNA or said foreign DNA can be inserted into a suitable restriction site of the CUP1 gene. For example, in order to prepare a yeast mutant deficient in all or part of the existing chromosomal CUP1 genes foreign DNA is inserted into a suitable restriction site occurring in the CUP1 gene. In case the yeast strain used has a defect in a chromosomal gene coding for an enzyme of amino acid or pyrimidine (e.g. uracile) biosynthesis a corresponding intact gene (such as URA3) can be inserted into the chromosomal CUP1 gene thus providing for prototrophy in the auxotrophic yeast strain and changing the genotype at the same time from CUP1 to cup1. The gene replacement or directed mutagenesis procedures are commonly applied in the art and are absolutely reproducible. In order to enhance the copper resistance of a given yeast strain (i.e. augmenting the number of chromosomal CUP1 genes) which is moderately resistant to copper said yeast strain can be subjected to higher copper concentrations in the medium causing an amplification of the CUP1 locus. Resulting surviving yeast cells contain more chromosomal CUP1 genes (for example 10–16) than the parent strain and can be isolated from the medium in a manner known per se.

A further current method to create yeast strains having a desired genetic background, for example having all or part of chromosomal CUP1 genes disrupted and/or having deficiencies in certain proteases, consists in meiotic crossing of suitable yeast strains and subsequent tetrad analysis. The tetrads, which derive from the diploid cells, are dissected according to standard genetic techniques. Random assortment among the four spores of a tetrad allows the construction of suitable mutants in subsequent crosses. Random spore analysis can also be used as an alternative system.

Yeast strains containing 1–3 additional copies of the chromosomal ACE1 gene can also be prepared in a conventional manner. For example, the ACE1 gene(s) can be inserted into appropriate restriction site(s) of chromosomal gene(s) conferring antibiotic resistance or in gene(s) involved in amino acid or purine or pyrimidine base synthesis rendering resulting yeast strains containing such additional copy (copies) of the ACE1 gene antibiotic sensitive and, respectively, auxotrophic with respect to the corresponding amino acid, purine or pyrimidine base.

BRIEF DESCRIPTION OF THE DRAWINGS

In the following experimental part various embodiments of the present invention are described with reference to the accompanying drawings in which.

The following abbreviations are used in the figures: term=PHO5 transcription terminator; p in CUP1p, GAPFLp and ACE1p=promoter.

The following examples illustrate the invention and should not be construed as a limitation thereof.

Experimental Part

Strains and plasmids

*E. coli* DH5αF':

*Escherichia coli* K12F' endA1 hsdR17(r$^-$m$^+$) supE44 thi1 recA1 pyrA relA1 PHI80lacZdelM15 del(lacZYA-argF) U169; Hanahan D. (1983) Studies on transformation of *Escherichia coli* with plasmids. J. Mol. Biol. 166:557 (Bethesda Research Laboratories).

*S. cerevisiae* H449:

*Saccharomyces cerevisiae* MATa, ura3Δ15, leu2-3, leu2-112, prb1, cps1, [cir$^0$]. DSM 4413; Feb. 18, 1988.

*S. cerevisiae* HT462/TH3:

MATα, cup1::URA3, kex1, prc1, leu2-3; leu2-212; DSM 7190; Jul. 22, 1992.

*S. cerevisiae* strain 55.6B:

MATa, his3, leu2, trp1, ura3-52, cup1::URA3; cf. Thiele, D. J. et al. Science 231 (1986), 854–856

Figure 3:
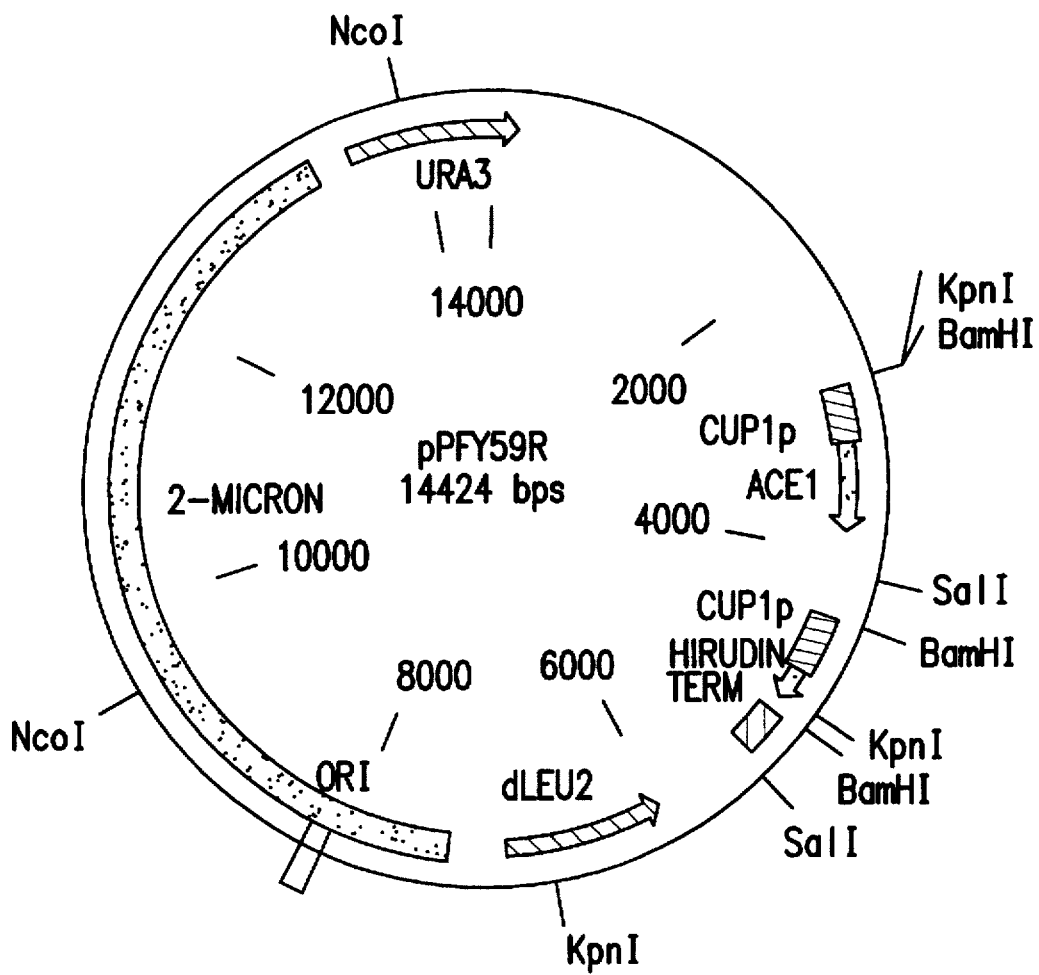
FIG. 3 is a schematic illustration of plasmid pPFY59R.

Plasmid pDP34:

EP-A-340 170, FIG. 3 therein; a yeast-*E. coli* shuttle vector with the ampicillin resistance marker for *E. coli* and the URA3 and dLEU2 yeast selective markers. It contains the complete 2 micron sequence in the A form and is REP1, REP2 and FLP proficient. DSM 4473; Mar. 14, 1988.

Plasmid pJDB207/GAPFL-YHIR:

A yeast plasmid for the expression of desulphatohirudin variant HV1 under the control of a short, constitutive promoter of the yeast glyceraldehyde-3-phosphate dehydrogenase (GAPDH) gene. The coding sequence of desulphatohirudin consists of preferred yeast codons; cf. EP-A-340 170

Plasmid pTZ18R:

Plasmid derived from pUC18 includes an M13 origin of replication so it can become single stranded and be packaged in M13 phage heads with the aid of a helper M13 phage. Mead D. A., Szczesna-Skompa E., Kemper B., Single stranded DNA 'blue' T7 promoter plasmids: a versatile tandem promoter system for cloning and protein engineering. Protein Engineering 1 (1986), 67–74. (Pharmacia).

Plasmid pFBY2:

This plasmid is constructed by inserting the 166 bp AluI fragment containing the FRT site from *S. cerevisiae* two micron plasmid between the HindIII and EcoRI sites of pTZ18R and the whole of the two micron plasmid cut with XbaI into the unique XbaI site of pTZ18R. DSM 6271; Dec. 14, 1990.

Plasmid pFBY4:

This plasmid consists of a 1.1 kb XbaI fragment containing the whole of the URA3 gene of S. cerevisiae cloned into the unique XbaI site of pTZ18R. This plasmid serves as a convenient source for a 1.1 kb URA containing XbaI fragment. DSM 6272; Dec. 14, 1990.

Plasmid pFBY5:

pFBY5 is derived from a large plasmid containing the whole of the S. cerevisiae two micron plasmid plus the URA3 and Leu2 genes of S. cerevisiae in the bacterial vector pUC18. Into the unique SalI site of this vector is inserted a 1.1 kbp SalI fragment containing an expression cassette consisting of a promoter derived from the S. cerevisiae GAPDH gene fused to the PHO5 signal sequence which in turn is fused to a synthetic hirudin encoding DNA fragment, which is followed by the PHO5 terminator. DSM 6273; Dec. 14, 1990.

Plasmid pFBY29:

This plasmid consists of a 2 kbp BamHI/SalI fragment containing the LEU2 gene. The fragment is inserted between the BamHI and SalI sites of pTZ18R. pFBY29 serves as a source of a 2.0 kbp fragment containing LEU2. DSM 6275; Dec. 14, 1990.

All DNA manipulations are—if not otherwise noted—carried out according to standard protocols (e.g. Maniatis, T. et al.: Molecular cloning: a laboratory manual. Cold Spring Harbor Laboratory, Cold Spring Harbor, N.Y. (1982).

EXAMPLE 1

Construction of plasmid pPFY56. A hybrid gene containing the CUP1 promoter, the PHO5 leader sequence and a synthetic hirudin gene In order to achieve inducible, high level expression of secreted desulphato-hirudin, DNA sequences coding for hirudin HV1 and for the PHO5 leader sequence are fused and placed under the control of the copper inducible CUP1 promoter.

pDP34 (cf. European Patent Application No. 340170, FIG. 3 therein) is a yeast-E. coli shuttle vector with the ampicillin resistance marker for E. coli and the URA3 and dLEU2 yeast selective markers. It contains the complete 2 micron sequence in the A form and is REP1, REP2 and FLP proficient. Plasmid pDP34 is digested with BamHI. The sticky ends of the restriction site are filled in a reaction with Klenow DNA polymerase (T. Maniatis et al., in: "Molecular Cloning. A Laboratory Manual", Cold Spring Harbor Laboratory, 1982). The DNA is further cut with SalI and the 11.8 kb vector fragment is isolated on a preparative 0.6% agarose gel. The DNA is recovered by electroelution and ethanol precipitation.

Plasmid pJDB207/GAPFL-YHIR (a yeast plasmid for the expression of desulphatohirudin variant HV1 under the control of a short, constitutive promoter of the yeast glyceraldehyd-3-phosphate dehydrogenase (GAPDH) gene; the coding sequence of desulphatohirudin consists of preferred yeast codons; cf. European Patent Application No. 340170) is digested with HindIII. The sticky ends are converted to blunt ends by Klenow DNA polymerase. The DNA is ethanol precipitated and further digested with SalI. The 1.1 kb SalI-[HindIII]/blunt end fragment contains the complete expression cassette with pBR322 sequences, the GAPFL promoter, the PHO5 signal sequence fused in frame to the coding sequence (preferred yeast codons) of desulphatohirudin and the PHO5 transcription termination fragment. The 1.1 kb fragment is isolated on a preparative 0.8% agarose gel, recovered from the gel by electroelution and purified by DE52 ion exchange chromatography and ethanol precipitation.

0.2 pmoles of the 1.1 kb fragment and 0.1 pmoles of the 11.8 kb vector fragment are ligated in 10 µl of 60 mM Tris-HCl pH 7.5, 10 mM MgCl$_2$, 5 mM DTT, 3.5 mM ATP and 400 units of T4 DNA ligase (Biolabs) for 16 h at 15° C. A one µl aliquot is used to transform E. coli HB101 Ca$^{2+}$ cells. 5 transformed, ampicillin resistant colonies are analysed. Plasmid DNA is digested with BamHI and SalI/BamHI. One clone with the correct restriction fragments is selected and referred to as pDP34/GAPFL-YHIR (for details, see European Patent Application No. 340170).

The synthetic hirudin gene, fused to the PHO5 leader sequence, is isolated from the plasmid pDP34/GAPFL-YHir as a 0.5 kb EcoR1 fragment that also contains PHO5 transcription termination sequences.

The CUP1 promoter (T. R. Butt et al. (1984) Proc. Natl. Sci U.S.A. 81, 3332–3336) is cloned from S. cerevisiae genomic DNA by polymerase chain reaction(PCR) using the PCR kit from Perkin Elmer and the following two oligonucleotides as primers:

5'- GGATCCATTACCGACATTTGGGCGCTAT     SEQ ID NO: 3
5'- GAATTCACAGTTTGTTTTTCTTAATATCTA    SEQ ID NO: 4

100 ng of yeast genomic DNA (isolated from yeast strain H449) is incubated in 0.1 ml with 2.5 units of Taq DNA-polymerase, 0.02 mM of each primer and 0.2 mM of dATP, dCTP, TTP and dGTP in 10 mM TRIS pH 8.3, 50 mM KCl, 1.5 mM MgCl2. The reaction is incubated for 30 cycles: 30 sec at 92° C., for 1 min at 42° C. and at 72° C. for 1 min. The CUP1 promoter fragment of 0.4 kb, after isolation, purification and restriction with BamHI and EcoRI, is inserted into BamHI and EcoRI cut pBR322.

The resulting plasmid pBR322-CUP1 is restricted with EcoR1. The 4.4 kb vector containing the CUP1 promoter is isolated, purified and ligated with the 0.5 kb hirudin fragment. E. coli HB101 is transformed with the resulting plasmid pPFY53. pPFY53 is tested for proper orientation of the hirudin fragment by digestion with Sal1. The 1082 bp BamH1/Sal1 fragment containing the CUP1 promoter, the PHO5 leader sequence, the hirudin gene and the PHO5 terminator is shown in SEQ ID NO:1.

Figure 1:
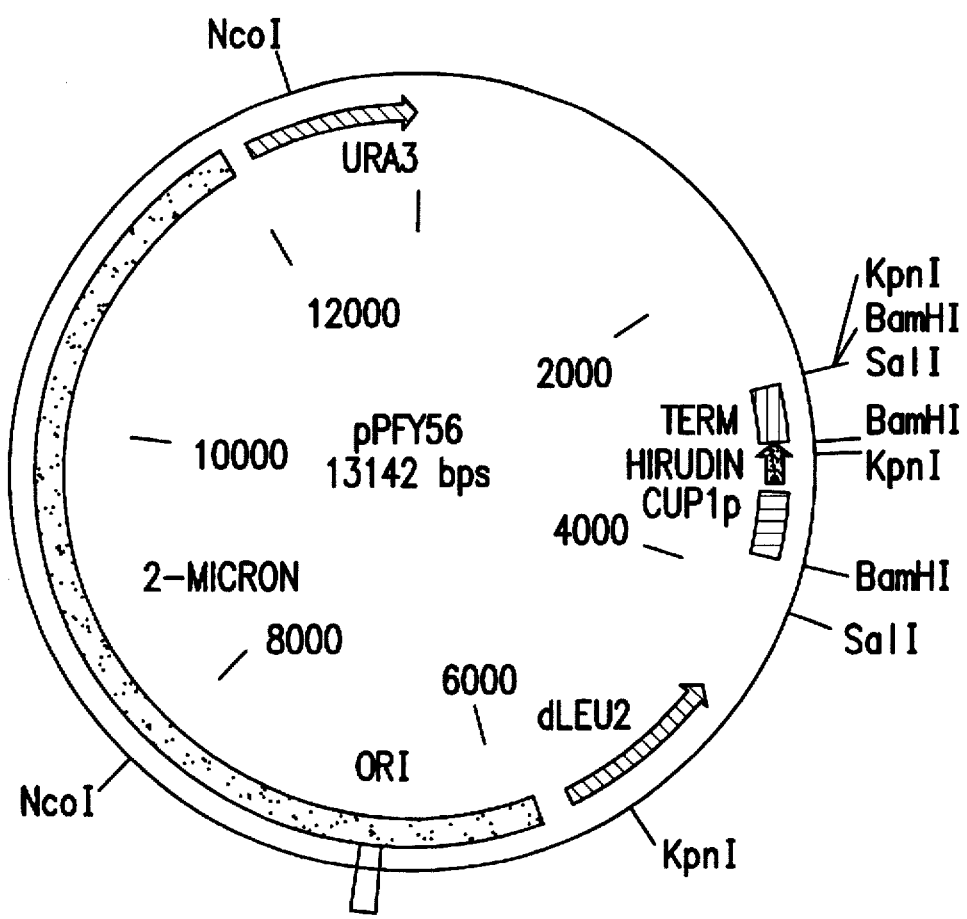
FIG. 1 is a schematic illustration of plasmid pPFY56.

The CUP1-hirudin expression cassette is isolated from pPFY53 as a 1.1 kb Sal1 fragment. This fragment is then inserted into Sal1 linearized pDP34. E. coli HB101 is transformed with the resulting plasmid pPFY56. The orientation is tested by digestion with KpnI. The transformed E. coli strain is designated E. coli/PFY56. pPFY56 is shown in FIG. 1.

EXAMPLE 2

Construction of plasmid pPFY58. Co-expression of hirudin from the CUP1 promoter and ACE1 from the ACE1 promoter The Ace1 protein is the copper responsive transcription factor that regulates CUP1 expression. It is constitutively expressed. Regulation occurs post-translationally.

The ACE1 gene (P. Fuerst et al., (1988) Cell 55, 705–717) is cloned from S. cerevisiae genomic DNA by polymerase chain reaction (PCR) using the PCR kit from Perkin Elmer and the following two oligonucleotides as primers:

5'- GATATCGATCGTGAAAGAATATTTGCT     SEQ ID NO: 5
5'- GATATCATGAGGATGATGACAAAGAAGAC    SEQ ID NO: 6

Figure 2:
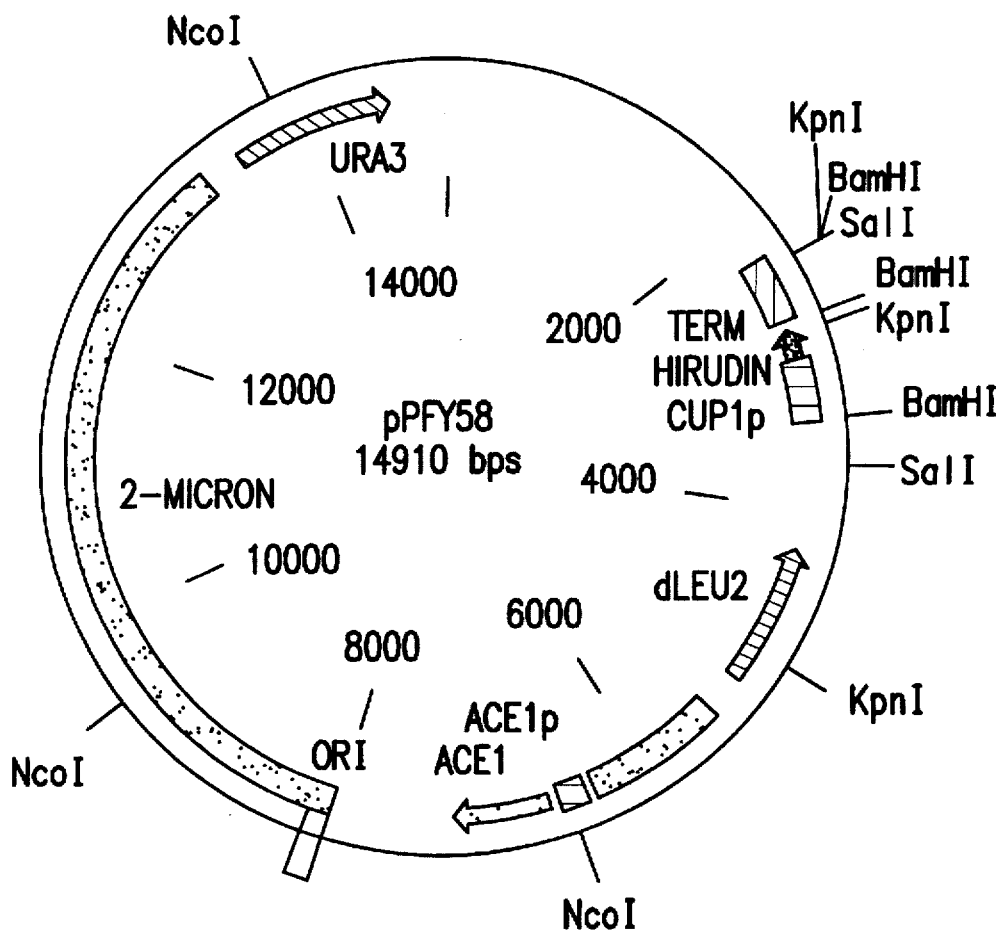
FIG. 2 is a schematic illustration of plasmid pPFY58.

100 ng of yeast genomic DNA is incubated in 0.1 ml with 2.5 units of Taq DNA-polymerase, 0.02 mM of each primer and 0.2 mM of dATP, dCTP, TTP and dGTP in 10 mM TRIS pH 8.3, 50 mM KCl, 1.5 mM MgCl2. The reaction is incubated for 30 cycles: 30 sec at 92° C., for 1 min at 42° C. and at 72° C. for 1 min. The ACE1 gene fragment of 1.7 kb, after isolation, purification and restriction with EcoRV, is inserted into the unique SnaB1 site of pPFY56 (example 1) leading to plasmid pPFY58 which is transformed into E. coli HB101. The orientation is tested by restriction with NcoI. The transformed E. coli strain is designated E. coli/PFY58. pPFY58 is shown in FIG. 2.

EXAMPLE 3

Construction of plasmid pPFY59R. Co-expression of desulphatohirudin from the CUP1 promoter and ACE1 from the CUP1 promoter In order to achieve tightly regulated, high level expression of ACE1 the constitutive ACE1 promoter present on the 1.7 kb EcoRV fragment (example 2) is exchanged to the CUP1 promoter. For fusion of ACE1 coding sequences to the CUP1 promoter an EcoR1 site up-stream of the ACE1 start codon is introduced by site directed mutagenesis.

The 1.7 kb EcoRV fragment (example 2) containing the ACE1 gene is subcloned into the EcoRV site of the vector pBluescriptKS+ (Stratagene, La Jolla, Calif., U.S.A.) to give plasmid pKSACE1. To introduce a new EcoR1 site by in vitro mutagenesis using the uracil-DNA method (Bio-Rad Muta-Gene M13 kit, Bio-Rad, Richmond, Calif., U.S.A.) the following oligonucleotide is used as a primer:

5'- CTGATAATCAGTGAATTCACAGAATG- 3'       SEQ ID NO: 7

First, pKSACE1 is transfected into E. coli CJ236 to incorporate uracil (Muta-Gene kit, supra). Single-stranded DNA from transfected CJ236 is isolated using M13 helper phage (Stratagene, supra).

200 pmoles of the oligonucleotide are phosphorylated in a volume of 0.03 ml containing 3 µl 1M Tris-HCl pH 8.0, 0.3 ul 1M MgCl$_2$, 0.75 µl 0.2M DTT, 0.6 µl 20 mM ATP and 5 units T4 polynucleotide kinase. The mixture is incubated at 37° C. for 60 min and at 65° C. for 15 min. The phosphorylated oligonucleotide is annealed to the template DNA as follows: 0.1 pmoles of uracil containing DNA derived from pKSACE1 are incubated with 2 pmoles of phosphorylated primer in 10 µl annealing buffer (20 mM Tris-HCl pH 7.5, 2 mM MgCl$_2$, 50 mM NaCl). The mixture is incubated for 10 min at 80° C. and then allowed to cool slowly to 25° C.

Subsequently the complementary strand is synthesized: 10 µl of the annealing reaction is incubated with 4 µl 2 mM dNTP's, 0.75 µl 0.5M Tris-HCl pH 7.5, 0.75 µl 0.1M MgCl$_2$, 2.2 µl 0.2M DTT, 1 unit of T4 DNA polymerase and 2 units of T4 DNA ligase. The reaction mixture is incubated on ice for 10 min, at 25° C. for 10 min and at 37° C. for 90 min. The resulting double-stranded DNA is transformed into E. coli JM101. Plasmids are prepared and analyzed for the correct EcoR1 site. One plasmid with the new EcoR1 site is designated pKSACE1-Eco.

The 1.5 kb EcoR1 fragment from pKSACE1-Eco which contains the ACE1 coding sequences and termination sequences without the ACE1 promoter is cloned into the EcoR1 site of the vector pBR322-CUP1 (example 1) to place ACE1 under CUP1 promoter control. The resulting plasmid pCup-ACE is transfected into E. coli HB101.

The 1.2 kb BamH1/SnaB1 fragment from pCup-ACE is ligated into the vector pDP34 linearized with BamH1. Ligation is carried out in 20 µl containing 10 fmoles of vector DNA linearized with BamH1, 30 fmoles of BamH1/SnaB1 fragment, 20 mM Tris pH 7.5, 5 mM MgCl2, 1 mM DTT, 0.1 mM ATP and 1 unit of T4 DNA ligase. After incubation for 60 min at 25° C. the molecules are blunt-ended in 50 µl containing 20 mM Tris-HCl pH 7.5, 5 mM MgCl$_2$, 1 mM DTT, 0.1 mM dNTP's and 1 unit of Klenow fragment of E. coli DNA polymerase. The mixture is incubated for 10 min at 37° C.

The blunt-ended molecules are then circularized by ligation in 100 µl containing 20 mM Tris-HCl pH 7.5, 5 mM MgCl2 1 mM DTT, 0.1 mM ATP and 1 unit of T4 DNA ligase for 18 hours at 15° C. The resulting plasmid pPFY54 is transfected into E. coli HB101 and tested for orientation by restriction with PvuII.

The 1.1 kb Sall fragment from pPFY53 containing the CUP1-hirudin expression cassette (example 1) is subcloned into the vector pPFY54 linearized with Sall. The derived plasmid pPFY59R is transfected into E. coli HB101. The orientation is tested by digestion with KpnI. The E. coli strain carrying pPFY59R is designated E. coli/PFY59R. pPFY59R is shown in FIG. 3.

EXAMPLE 4

Construction of pPFY79. Desulphatohirudin expression from two different promoters To enhance the levels of hirudin mRNA, hirudin coding sequences can be simultaneously expressed from two different promoters.

Figure 4:
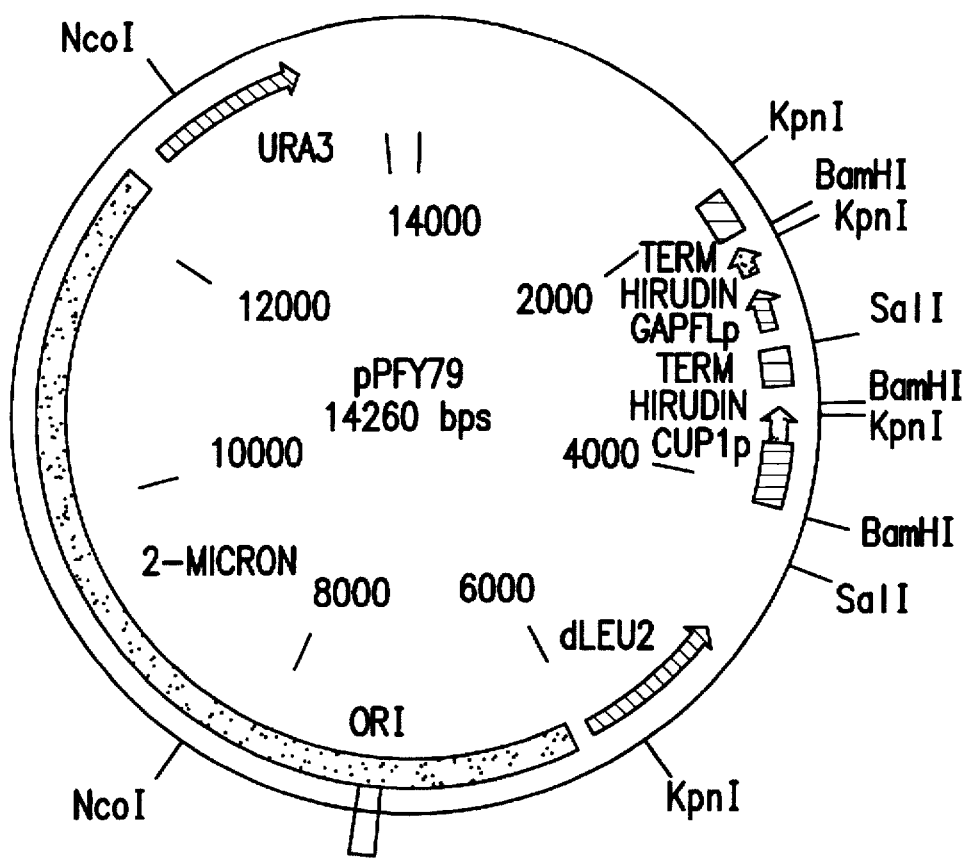
FIG. 4 is a schematic illustration of plasmid pPFY79.

The CUP1-hirudin expression cassette is isolated as a 1.1 kb Sall fragment from plasmid pPFY53 (example 1). This fragment is cloned into the unique Sall site of the vector pDP34/GAPFL-YHir. The orientation of the Sall fragment in the resulting plasmid pPFY79 is tested by restriction with BamH1. E. coli HB101 transfected with pPFY79 is designated E. coli/PFY79. pPFY79 is shown in FIG. 4.

EXAMPLE 5

Transformation of Saccharomyces cerevisiae strain Tr1456 with plasmids pPFY56, pPFY58, pPFY59R, pPFY79 and pDP34-GAPFL-YHir Saccharomyces cerevisiae strain Tr1456 is constructed as disclosed in European Patent Application No. 341215. Starting with Saccharomyces cerevisiae strain H449, in two subsequent series of experiments the two carboxypeptidases yscα and yscY are removed from strain H449 by disruption of their encoding genes KEX1 and PRC1, respectively. First, the gene encoding yscα, KEX1, is disrupted. For this purpose, strain H449 is transformed with a DNA fragment encoding the KEX1 gene, with the full URA3 gene inserted in the middle of the KEX1 coding region. Uracil prototrophic transformants are selected and tested for the absence of yscα activity. Next, the URA3 gene inserted at the KEX1 locus is disrupted by transformation with a plasmid containing a disrupted version of the URA3 gene, ura3Δ (see European Patent Application No. 341215). Transformants which are ura3 auxotrophic are selected and in the following step disrupted in their endogenous PRC1 gene coding for the carboxypeptidase yscY. The experiment is carried out in a totally analogous manner as described for the disruption of KEX1. The finally resulting isogenic derivative of strain H449 is called Tr1456 and has the following genotype:

Tr1456=MATa, leu2-3,112, ura3, prb1, kex1::ura3, prc1::ura3, [cir⁰]

Transformation of strain Tr1456 with plasmids pDP34/GAPFL-YHir, pPFY56, pPFY58, pPFY59R and pPFY79 is done according to Dohmen et al. [1989, Curr. Genet. 15, 319–325]. Transformed yeast cells are selected on yeast minimal media plates supplemented with leucine and deficient in uracil. Single transformed yeast clones are isolated and referred to as:

Saccharomyces cerevisiae Tr1456/pDP34/GAPFL-YHir
Saccharomyces cerevisiae Tr1456/pPFY56
Saccharomyces cerevisiae Tr1456/pPFY58
Saccharomyces cerevisiae Tr1456/pPFY59R
Saccharomyces cerevisiae Tr1456/pPFY79

EXAMPLE 6

Desulphato-hirudin expression in minimal medium under different copper concentrations Cells of Saccharomyces cerevisiae Tr1456/pPFY56, Saccharomyces cerevisiae Tr1456/pPFY58 and Saccharomyces cerevisiae Tr1456/pPFY59R are each grown in two subsequent cultures composed of (g/l):

| Difco Yeast Nitrogen Base (without aminoacids) | 6.7 |
|---|---|
| L-asparagine | 10 |
| L-histidine | 1 |
| L-leucine | 0.1 |
| glucose | 20 |

The first cultures are grown for 60 h at 30° C. and 180 r.p.m. The second cultures are inoculated with 2% (volume per volume) of the first cultures and grown for 24 h at 30° C. and 180 r.p.m. After 24 h the cultures are centrifuged, the cells washed once with saline and resuspended in the original volume of fresh medium (see above) to which different concentrations of copper sulphate are added. The cells are grown for another 24 h at 30° C. and 180 r.p.m., afterwards the cells removed by centrifugation and the amount of desulphato-hirudin in the supernatant measured by HPLC as disclosed in patent application 340170. The results are summarized in Table 1.

TABLE 1

Desulphatohirudin expression in minimal medium

| | Desulphatohirudin (mg/l) Concentration of copper sulphate (mM) | | | | |
|---|---|---|---|---|---|
| | 0 | .05 | .125 | .25 | .4 |
| Tr1456/pPFY56 | 2 | 1 | 20 | 20 | 11 |
| Tr1456/pPFY58 | 8 | 24 | 20 | 12 | 3 |
| Tr1456/pPFY59R | 3 | 23 | 23 | 10 | 1 |

Under the conditions chosen, desulphatohirudin is expressed in all transformants containing one of the plasmid constructions. Expression is strictly copper dependent, as in the absence of added copper very little desulphato-hirudin is found. Optimal copper concentration under those conditions are between 0.05 and 0.25 mM.

EXAMPLE 7

Comparison of desulphatohirudin titers under control of the GAPFL-promoter as opposed to the CUP1-promoter in complex medium Previously, as disclosed in European Patent Application No. 340170, desulphatohirudin expression had been optimized in rich, complex medium under control of a short fragment of the strong GAPDH promoter. Therefore, CUP1-promoter containing plasmids are compared under those previously disclosed conditions, ±copper addition. In addition, the optimal time point for copper addition is determined.

Cells of Saccharomyces cerevisiae TR1456/pPFY56, or TR1456/pPFY58, or TR1456/pPFY59R, or TR1456/pDP34/GAPFL-YHir are each grown in two subsequent precultures in 20 ml synthetic medium composed of (g/l):

| Difco Yeast Nitrogen Base (without amino acids) | 6.7 |
|---|---|
| L-asparagine | 10 |
| L-histidine | 1 |
| L-leucine | 0.1 |
| glucose | 20 |

The pH of the medium is adjusted to 5.8. The first preculture is grown for 60 h at 28° C. and 180 r.p.m. The second preculture is inoculated with 2% (volume per volume) of the first preculture and incubated for 24 h at 28° C. and 180 r.p.m. The medium of the main culture is composed of (g/l):

| peptone | 5 |
|---|---|
| yeast extract | 10 |
| glucose | 20 |
| sucrose | 40 |
| ammonium sulphate | 3 |
| potassium dihydrogenphosphate | 2 |
| magnesium sulphate heptahydrate | 0.5 |
| sodium chloride | 0.1 |
| calcium chloride | 0.1 |
| biotin | 10–5 |

The main culture (100 ml medium) is inoculated with about 2×10⁶ cells/ml and incubated for 96 h at 28° C. and 180 r.p.m. Sterile copper sulphate at a concentration of 200 NM is added to the main cultures either 0 h, or 7 h, or 11 h, or 14 h, or 24 h after inoculation of the main culture. At the end of the fermentation aliquots of the cultures are taken, the cells are removed by centrifugation and the culture supernatant is analysed for desulphatohirudin as described above. The results are shown in the following table 2.

TABLE 2

Influence of the time point of promoter induction on the CUP1-directed production of desulphatohirudin in complex medium

| | Desulphatohirudin secretion (mg/l) Time point of copper addition (h after inoculation of the main culture) | | | | | |
|---|---|---|---|---|---|---|
| Strain/plasmid | 0 | 7 | 11 | 14 | 24 | control* |
| TR1456/pPFY56 | 123 | 104 | 79 | 71 | 72 | 10 |
| TR1456/pPFY58 | 185 | 170 | 143 | 94 | 100 | 13 |
| TR1456/pPFY59R | 146 | 117 | 88 | 95 | 105 | 18 |
| TR1456/pDP34/GAPFL-YHir | 127 | 131 | 135 | 121 | 105 | 111 |

*no copper sulphate added to the main culture

The highest expression of desulphatohirudin from the CUP1-promoter is obtained when the promoter is used in a "pseudo-constitutive" way (i.e., the promoter induction occurs together with the inoculation of the main culture) and when the ACE1-gene is present on the plasmid that contains the hirudin expression-cassette. Unexpectedly, under the induction conditions that are disclosed here, higher titers of hirudin are obtained with strains S. cerevisiae TR1456/pPFY58 and TR1456/pPFY59R than with strain S. cerevisiae TR1456/pDP34/GAPFL-YHir that contains a hirudin expression cassette under the control of an improved version of the strong constitutive GAPDH-promoter.

EXAMPLE 8

Optimisation of the copper concentration for CUP1-directed secretion of desulphatohirudin in complex medium Cells of Saccharomyces cerevisiae TR1456/pPFY56, or TR1456/pPFY58, or TR1456/pPFY59R, or TR1456/pDP34/GAPFL-YHir are each grown in two subsequent precultures in 20 ml synthetic medium as described in the previous section. The main culture is grown in the complex medium described above and is inoculated with about 2×106 cells/ml and incubated for 96 h at 28° C. and 180 r.p.m. Immediately following the inoculation of the main cultures, sterile copper sulphate at the following concentrations is added to the medium: 0 µM, or 50 µM, or 200 µM, or 500 µM, or 1 mM, or 2.5 mM, or 5 mM. At the end of the fermentation aliquots of the cultures are taken, the cells are removed by centrifugation and the culture supernatant is analysed for desulphatohirudin as described above. The results are shown in the following table 3.

TABLE 3

Influence of the concentration of copper sulphate on CUP1-directed secretion of desulphatohirudin HV1

| Strain/plasmid | Desulphatohirudin secretion (mg/l) concentration of copper sulphate in the medium (µM) | | | | | | |
|---|---|---|---|---|---|---|---|
| | 0 | 50 | 200 | 500 | 1000 | 2500 | 5000 |
| TR1456/pPFY56 | 8 | 70 | 113 | 176 | 236 | 182 | 35 |
| TR1456/pPFY58 | 11 | 159 | 169 | 168 | 174 | 177 | 38 |
| TR1456/pPFY59R | 22 | 100 | 130 | 194 | 233 | 129 | 46 |
| TR1456/pDP34/ GAPFL-YHir | 128 | 125 | 120 | 123 | 136 | 119 | 26 |

At optimal copper concentrations, considerably higher titers of desulphato-hirudin are obtained when a CUP1-YHir expression cassette is used than when the hirudin expression cassette is under the control of the strong constitutive GAPFL-fragment of the GAPDH-promoter. At copper sulphate concentrations below 200–500 µM, plasmids pPFY58 and pPFY59R that contain the gene of the transcriptional activator ACE1 are superior to plasmid pPFY56 that is devoid of the ACE1 gene.

EXAMPLE 9

Construction of plasmid pDP34/[GAPFL-HIR]D with two hirudin expression cassettes in a tandem array Plasmid pDP34/[GAPFL-HIR]D comprises a DNA insert which consists of two hirudin expression cassettes in a tandem head to tail arrangement. The two cassettes are identical and contain the coding sequence of the PHO5 signal sequence and desulphato-hirudin HV1 under the control of a short, constitutive GAP49 (TDH3) promoter (GAPFL) and the PHO5 transcription terminator. Plasmid pJDB207/[GAPFL-HIR]D has the tandem expression cassette in yeast vector pJDB207. This construction is described in EP 225633.

pJDB207/[GAPFL-HIR]D is cut a the unique HindIII site. The sticky ends of the restricted sites are converted to blunt ends by Klenow DNA polymerase. Partial SalI digestion in the presence of 0.01 mg/ml of ethidiumbromide allows the isolation of the 2.1 kb SalI-blunt-end fragment with the two expression cassettes. Plasmid pDP34 (see Example 1) is cut with BamH1, treated with Klenow DNA polymerase and digested with SalI The isolated large vector fragment is used to clone the 2.1 kb SalI-blunt-end fragment. A correct clone is referred to as pDP34/[GAPFL-HIR]D with the tandem cassettes cloned in an anticlockwise orientation.

EXAMPLE 10

Comparison of desulphatohirudin titers obtained using plasmids with one or two hirudin expression cassettes, respectively Cells of Saccharomyces cerevisiae TR1456/pPDP34/GAPFL-YHir, or TR1456/pPFY56, or TR1456/pPFY79, or TR1456/pDP34/[GAPFL-HIR]D are each grown in two subsequent precultures followed by a main culture as described in Example 7. The main culture is inoculated with about 2×106 cells/ml and incubated for 96 h at 28° C. and 180 r.p.m. Immediately after inoculation of the main culture, sterile copper sulphate at a concentration of 0 µM, or 50 µM, or 200 µM, or 500 µM, or 750 µM, or 1 mM, or 2.5 mM is added. At the end of the fermentation aliquots of the cultures are taken, the cells are removed by centrifugation and the culture supernatant is analysed for desulphatohirudin by HPLC. The results are shown in the following table 4:

TABLE 4

| strain/plasmid | Desulphatohirudin secretion (mg/l) concentration of copper sulphate in the medium (µM) | | | | | | |
|---|---|---|---|---|---|---|---|
| | 0 | 50 | 200 | 500 | 750 | 1000 | 2500 |
| TR1456/pPFY56 | 5 | 86 | 118 | 164 | 188 | 236 | 63 |
| TR1456/pPFY79 | 90 | 158 | 151 | 192 | 214 | 233 | 93 |
| TR1456/pDP34/ [GAPFL-HIR]D | 96 | n.d. | 84 | n.d. | n.d. | 102 | n.d. |
| TR1456/pDP34-GAPFL-YHir | 94 | n.d. | 88 | n.d. | n.d. | 98 | n.d. | n.d. = not determined

Under the condition of the experiment, plasmid pPFY79 that contains a constitutive GAPFL-YHir expression cassette and a second, copper-inducible CUP1-YHir expression cassette is superior to 1.) a plasmid, such as pPD34/GAPFL-YHir, that contains only a constitutive expression cassette, or 2.) to a plasmid, such as pPFY56/CUP1-Hir that contains only a copper-inducible expression cassette, or 3.) to a plasmid, such as pDP34/GAPFL-YHir+GAPFL-YHir that contains two constitutive expression cassettes.

EXAMPLE 11

Construction of a copper-resistant isogenic derivative of Saccharomyces cerevisiae strain Tr1456

Saccharomyces cerevisiae strain Tr1456 is—as most laboratory yeast strains—a strain which is moderately resistant to the addition of copper to the medium. This resistance is due to the presence of a 2 kb segment of chromosomal DNA which contains approximately 3 copies of the endogenous CUP1 locus [D. Hamer, et al. Science 228 (1985), 685–690]. In the presence of large amounts of copper in the medium, even higher resistant derivatives are obtained which are due to tandem reiteration of the above mentioned 2 kb CUP1-containing chromosomal DNA segment. To construct such a higher resistant derivative, S. cerevisiae Tr1456 is inoculated into the synthetic minimal medium as disclosed in Example 6, supplemented with 1.2 mM copper sulphate. The culture is grown for 8 days at 30° C. and 180 r.p.m. The culture is then plated out on synthetic minimal medium without copper addition at a suitable density to obtain single colonies. DNA from selected individual colonies is prepared, digested with EcoR1, separated on agarose gels and analysed for the presence and length of the CUP1 locus by Southern blotting. Experimental conditions are according to Hamer et al. [see above]. One colony with a shift in the electrophoretic mobility of the CUP1 locus indicative for the presence of at least 10 copies of the CUP1 locus is selected and referred to as *S. cerevisiae* strain Tr1631.

EXAMPLE 12

Transformation of *S. cerevisiae* strain Tr1631 with plasmids pPFY56, pPFY58, and pPFY59R Transformation of *S. cerevisiae* strain Tr1631 with plasmids pPFY56, pPFY58, pPFY59R is done as described above. Single transformed yeast clones are isolated and referred to as:

*Saccharomyces cerevisiae* Tr1631/pPFY56,
*Saccharomyces cerevisiae* Tr1631/pPFY58 and
*Saccharomyces cerevisiae* Tr1631/pPFY59R

EXAMPLE 13

Comparison of the transformed copper-resistant *S. cerevisiae* strain Tr1631 with transformed strain Tr1456 at higher copper concentrations Cells of *S. cerevisiae* Tr1631/pPFY56, *S. cerevisiae* Tr1631/pPFY58, *S. cerevisiae* Tr1631/pPFY59R and cells of *S. cerevisiae* Tr1456/pPFY56, *S. cerevisiae* Tr1456/pPFY58, *S. cerevisiae* Tr1456/pPFY59R are cultivated as described in Examples 7 and 8. To the main culture 0, 0.5 mM, 1 mM, 2 mM or 4 mM copper sulphate are added immediately after inoculation of the main culture. The cultures are grown for 72 h at 30° C. and 180 r.p.m. At the end of the fermentation aliquots of the cultures are taken, the cells are removed by centrifugation and the culture supernatant is analysed for desulphato-hirudin by HPLC. The results are shown in table 5.

TABLE 5

Comparison of transformed strain Tr1631 with transformed strain Tr1456

| Strain | Desulphatohirudin (mg/l) Concentration of copper sulphate (mM) | | | | |
|---|---|---|---|---|---|
| | 0 | 0.5 | 1 | 2 | 4 |
| Tr1631/pPFY56 | 7 | 115 | 165 | 154 | 83 |
| Tr1631/pPFY58 | 6 | 106 | 115 | 124 | 103 |
| Tr1631/pPFY59R | 18 | 131 | 163 | 165 | 87 |
| Tr1456/pPFY56 | 5 | 184 | 239 | 87 | 39 |
| Tr1456/pPFY58 | 6 | 146 | 132 | 133 | 43 |
| Tr1456/pPFY59R | 12 | 160 | 221 | 166 | 37 |

The results show superior productivity of desulphatohirudin in transformed copper-resistant strain *S. cerevisiae* Tr1631 at higher copper concentrations in the culture medium.

EXAMPLE 14

Crossing of *S. cerevisiae* strain 55.6B (cup1::URA3) with *S. cerevisiae* strain TR1456 and analysis of the spores with respect to copper sensitivity The *S. cerevisiae* strain 55.6B (MATa his3 leu2 trp1 ura3-52, cup1::URA3; cf. Thiele, D. J. et al. Science 231 (1986), 854–856) that is deleted in the CUP1 locus is crossed with strain TR1456 (MATa leu2-3,212, ura3D5 kex1 prb1 prc1) that carries approximately 3 copies of the CUP1 locus (i.e. 6 copies of the tandemly arranged CUP1 gene). Diploid heterozygous cells of the genotype cup1::URA3/CUP1 are isolated from this cross. The tetrads which are derived from the diploid cells are dissected according to standard genetic techniques [Methods in Yeast Genetics 1986 (Sherman F., Fink G. R., Hicks J. B., eds.) Cold Spring Harbor Laboratory, New York]. The descendants of the four spores of every tetrad are tested for their ability to grow on YPD agar plates (10 g yeast extract, 20 g peptone, 20 g glucose and 25 g agar per liter of double distilled water) supplemented with either 0 μM, 250 μM, 500 μM or 1 mM copper sulphate. Spores that inherit the intact CUP1 gene give rise to progeny that grows vigorously on copper agar, whereas spores that inherit the disrupted cup1::URA3 gene give rise to progeny that grows poorly on copper agar. The descendents of two copper sensitive spores of several complete tetrads are tested for their ability to mate with strain TR1456. The descendents of a spore of the appropriate mating type are crossed with TR1456 and diploid heterozygous cells of the genotype cup1::URA3/CUP1 are isolated from this cross. The tetrads which are derived from the diploid cells are dissected and the spores are tested for sensitivity to copper sulphate as described above. The copper sensitive colonies obtained from approximately 50 complete tetrads are tested for growth on SD agar (6.7 g Bacto Yeast Nitrogen Base without amino acids, 20 g glucose and 25 g agar per liter of water), and on SD agar supplemented with 200M leucine. Colonies that do not grow on the SD plates but that do grow on SD agar supplemented with 200M leucine have the genotype cup1::URA3,HIS3,TRP1,leu2-3, 212 and are selected for further work.

EXAMPLE 15

Classification of confirmed cup1::URA3 mutants on additional deficiency of protease yscY and protease yscalpha and transformation of mutants

*S. cerevisiae* cup1::URA3 mutants obtained as disclosed under example 14 are further classified with regard to the deficiency of proteases encoded by the KEX1 and PRC1 genes. Colonies deficient in the KEX1 gene are identified on the basis of their reduced ability to secrete a-factor. A detailed description of the procedure used to discriminate between colonies carrying a wild type KEX1 gene and colonies mutated in the kex1 gene can be found European Patent Application No. 341215, example 1 therein. Colonies deficient in the PRC1 gene are identified by means of a biochemical test that measures the proteolytic activity of the product of the PRC1 gene, namely protease yscY. This test has been described in EP 341215. A single colony of the genotype cup1::URA3 kex1 prc1 leu2-3,212 is picked and is referred to as *Saccharomyces cerevisiae* HT462/TH3. Cells of strain HT462TH3 are transformed with either plasmid pDP34/GAPFL-YHIR, or plasmid pPFY56, or plasmid pPFY58, or plasmid pPFY59R, respectively. The method used for transformation has been disclosed in EP 341215. Single transformed yeast colonies containing either plasmid pPFY56, or plasmid pPFY58, or plasmid pPFY59R or plasmid pDP34-GAPFL-YHIR are picked. One transformed colony of every type is chosen for further work and is referred to as

*Saccharomyces cerevisiae* TH3/pPFY56,
*Saccharomyces cerevisiae* TH3/pPFY58,

Saccharomyces cerevisiae TH3/pPFY59R, and
Saccharomyces cerevisiae TH3/pDP34/GAPFL-YHIR, respectively.

EXAMPLE 16

Fermentation of transformed strain TH3 on a laboratory scale

Cells of Saccharomyces cerevisiae TH3/pDP34/GAPFL-YHIR, or Saccharomyces cerevisiae TH3/pPFY56, or Saccharomyces cerevisiae TH3/pPFY58 are each grown in two subsequent precultures of 20 ml synthetic medium as described in example 7. The main culture is grown on the complex medium disclosed in example 7. It is inoculated with about 2×106 cells/ml and incubated for 66 h at 28° C. and 180 r.p.m. Immediately following the inoculation of the main cultures, sterile copper sulphate at the following concentrations is added to the medium: 0 µM, 5 µM, 10 µM, 25 µM, 50 µM, 100 µM, 500 µM. At the end of the fermentation aliquots of the cultures are taken, the cells are removed by filtration and the culture supernatant is analysed for desulphatohirudin by HPLC. The results are shown in the following table 6:

TABLE 6

| | desulphatohirudin secretion (mg/l) concentration of copper sulphate in the medium (µM) | | | | | | | |
|---|---|---|---|---|---|---|---|---|
| Strain/plasmid | 0 | 5 | 10 | 25 | 50 | 100 | 200 | 500 |
| TH3/pPFY56 | 99 | 106 | 103 | 105 | 104 | 95 | 85 | 34 |
| TH3/pPFY58 | 110 | 117 | 110 | 112 | 113 | 107 | 95 | 113 |
| TH3/pDP34/ GAPFL-YHIR | 75 | 77 | 73 | 71 | 73 | 66 | 53 | 41 |

In a host strain, such as TH3, whose chromosomal copy of the CUP1 gene has been deleted, the best production of hirudin is obtained when a plasmid is introduced that contains, in addition to the CUP1-YHir expression cassette, a copy of the ACE1 gene under the ACE1 promoter. The optimal concentration of copper sulphate for promoter induction is considerably lower than when a strain containing 3 or more copies of the CUP1 locus is used.

EXAMPLE 17

Production of desulphatohirudin variant HV1 on a 50 L scale

A working cell bank of the transformed strain Saccharomyces cerevisiae Tr1456/pPFY56 or strain Saccharomyces cerevisiae Tr1456/pDP34/GAPFL-YHIR is used as a source of inoculum for the production of desulphatohirudin on a 50 L scale.

Ampoules of the working cell bank are preserved in the vapour phase in a liquid nitrogen container. The contents of one ampoule are used to inoculate a shake flask culture comprising a selective medium consisting of (g/L)

| | |
|---|---|
| yeast nitrogen base | 8.4 |
| L-asparagin monohydrate | 11.4 |
| L-histidin | 1.0 |
| L-leucine | 0.1 |
| D-glucose monohydrate | 20.0 |

The 500 mL flask contains 100 mL medium and is incubated for 48 h at 28° C. on an orbital shaker at a shaking speed of 180 rev/min.

The second shake flask pre-culture comprises of the same medium of which 600 mL are contained in a 2 L flask which has four baffles. The inoculum level from the first pre-culture is 5% (30 mL) and the flasks are incubated for 48 h at 28° C. on an orbital shaker at a speed of 120 rev/min.

A third pre-culture is fermented in a 50 L stainless steel bioreactor equipped with 4 baffles and a single disk turbine agitator with a diameter of 115 min. The above medium is also used for this culture, the starting volume being 30 L. A single 2 L flask containing 600 mL culture is used to inoculate the 50 L bioreactor (2.5%). The fermentation lasts for 48 h at a temperature of 28° C. The stirrer speed is 600 rev/min, aeration rate 0.5 vvm and the reactor is operated with an overpressure of 0.3 bar.

A similar 50 L bioreactor, additionally equipped for fed-batch processes, is used for the desulphatohirudin production stage. A medium consisting of (g/L)

| | |
|---|---|
| meat peptone (Merck) | 6.0 |
| yeast extract | 37.5 |
| ammonium sulphate | 6.0 |
| magnesium sulphate heptahydrate | 1.0 |
| sodium chloride | 0.1 |
| potassium dihydrogenphosphate | 4.0 | is used for this stage. The starting volume is reduced to 24 L to compensate for the glucose monohydrate solution which is added during the fermentation. The inoculum level from the third preculture stage is 2.5%. The fermentation lasts for 78 h at a temperature of 28° C. and the stirrer speed is set at 900 rev/min. The overpressure is initially set at 0.3 bar and is increased after 48 h to 1.0 bar. The initial air flow is 0.25 vvm but this is increased to 0.5 vvm after 9 h, to 0.75 vvm after 24 h and finally further increased to 1.0 vvm after 48 h. Increase of overpressure and aeration rate during the course of fermentation is done to ensure an adequate oxygen supply and to maintain the dissolved oxygen tension above 20% air saturation.

Subsequent after inoculation 10 g copper sulphate pentahydrate, dissolved in 500 mL deionized water, are added to the culture to initiate the expression of the desulphatohirudin which is under the control of the CUP1 promotor.

The pH value falls during the early part of the fermentation to a value of 5.0 at which it is maintained by an automatic feed of ammonium hydroxide. To avoid excessive production of ethanol by the growing yeast cells, a concentrated glucose monohydrate solution (70% w/v) is fed with a constant initial rate of 60 mL/h. After 18 h the feed rate is linearly increased with a factor of 5 mL/h reaching a final value of 360 mL/h at the end of the fermentation. This limited supply of the carbon source (fed-batch technology) supports a considerably higher final biomass concentration and desulphatohirudin titer than it is possible with a simple batch culture.

Small additions of a silicone based antifoam are used to control foaming when necessary. A portion of the exit gas from the bioreactor is analysed on-line to provide information about the oxygen uptake and carbon dioxide evolution rate. The dissolved oxygen tension is also measured on-line using a sterilizable Clark type electrode.

With 6 hourly intervals samples are withdrawn throughout the fermentation and are measured for the optical density (OD) and analysed for glucose, ethanol, phosphate and magnesium. The desulphatohirudin titer is monitored by HPLC. At the end of the fermentation the secreted desulphatohirudin are recovered from the culture supernatant. The fermentation titer of S. cerevisiae strain Tr1456/pPFY56 is compared with an identical fermentation of S. cerevisiae strain Tr1456/pDP34/GAPFL-YHIR, without copper addition. The results are shown in table 7.

TABLE 7

Comparison between the constitutive (GAPFL-Hir) and the regulated (CUP1-Hir) expression of desulphatohirudin in strain Tr1456. OD: optical density; sp. Hir: specific desulphatohirudin production.

| | 1456/pDP34-GAPFL-YHIR | | | 1456/pPFY56 | | |
|---|---|---|---|---|---|---|
| time (h) | OD | Hirudin (mg/L) | sp. Hir (mg/OD) | OD | Hirudin (mg/L) | sp. Hir (mg/OD) |
| 24 | 17 | 78 | 4.59 | 21 | 61 | 2.90 |
| 30 | 37 | 166 | 4.49 | 49 | 220 | 4.49 |
| 36 | 64 | 289 | 4.52 | 76 | 319 | 4.20 |
| 42 | 86 | 421 | 4.90 | 94 | 541 | 5.76 |
| 48 | 99 | 519 | 5.24 | 114 | 613 | 5.38 |
| 54 | 142 | 613 | 4.32 | 120 | 901 | 7.51 |
| 60 | 142 | 746 | 5.25 | 138 | 1234 | 8.94 |
| 66 | 144 | 835 | 5.80 | 129 | 1442 | 11.18 |
| 72 | 149 | 891 | 5.98 | 128 | 1654 | 12.92 |
| 78 | — | — | — | 137 | 1793 | 13.09 |

With the CUP1 system not only the final titer of desulphatohirudin but also the specific productivity of desulphatohirudin is considerably improved compared to the constitutive GAPFL-YHIR system.

EXAMPLE 18

Isolation and purification of desulphatohirudin variant HV1 produced on a 50 L scale Desulphatohirudin is isolated from the culture broth of a 50 L fermentation using yeast strain Tr1456/pPFY56 (see example 17). In-process controls are carried out monitoring the purity by reversed phase high performance liquid chromatography and analytical anionic exchange chromatography. The obtained data are compared with the results of a 50 L fermentation using yeast strain Tr1456/pDP34-GAPFL-YHir.

After termination of the fermentation the pH is adjusted to about 3, and the culture broth loaded on a hydrophobic polymeric resin. The resin with the adsorbed desulphatohirudin is washed with 1M NaCl solution and eluted with ammonium acetate buffer. In the fraction containing the protein activity, the pH (pH 3) and the conductivity are adjusted. Desulphatohirudin is then further purified using cationic exchange chromatography (Macro-Prep S, Biorad) followed by ultrafiltration. To remove high molecular weight compounds and colored impurities gel filtration is applied. After adjusting the pH to 5, the desulphatohirudin containing fraction is chromatographed on an anionic exchange resin (Macro-Prep Q, Biorad). The obtained desulphatohirudin solution is analysed for purity by reversed phase HPLC and anionic exchange chromatography. The copper content is determined using plasma emission spectroscopy.

The experimental data indicate that production of desulphatohirudin with strain Tr1456/pPFY56 leads to an at least equal desulphatohirudin quality regarding HPLC and FPLC purity as if produced with strain Tr1456/pDP34-GAPFL-YHir. With the higher titers obtained in the copper induced fermentation increased yields of desulphatohirudin for the downstream processing are obtained. The addition of copper to the fermentation medium causes no significant change in the by-product pattern. The data show that copper can easily be removed down to low ppm levels.

EXAMPLE 19

Construction of pFBY23

2 lag of pFBY2 is cleaved to completion by FspI in CA buffer (20 mM Tris(hydroxymethyl)aminomethane; 7 mM $MgCl_2$; 5 mM dithiothreitol; 100 mM KCl; HCl to pH 7.5). The restriction endonuclease is inactivated by heating at 65° C. for 10 min. The volume is doubled by the addition of water and the DNA fragments are blunt ended with 1 unit of T4 polymerase in the presence of 0.05 mM each of dATP, dCTP, dGTP and dTTP for 30 min at 37° C. The enzyme is heat inactivated at 65° C. for 10 min. After ethanol precipitation the DNA is recut with HindIII and EcoRI. These fragments are separated on a 2% LGT gel (Low gelling temperature agarose) in TAE buffer (40 mM Tris (hydroxymethyl)aminomethane; 2 mM Ethylenediaminetetraacetic acid (disodium salt) Acetic acid to pH 7.6). The 170 bp and the 523 bp fragments are cut out and the DNAs are purified by ElutipD® chromatography.

2 μg of pTZ18R is cleaved to completion by EcoRI and HindIII in CA buffer. These fragments are separated on a 0.8% LGT gel in TAE buffer. The 2.8 kbp band is cut out and the DNA is purified by ElutipD® chromatography.

Approximately 20 ng of each of the prepared fragments are ligated together with 10 pM of an unphosphorylated BamHI linker of the sequence GGGATCCC and 1 mM ATP and ligation buffer by 0.5 units of T4 ligase for 3 h at room temperature.

This ligation mixture is used to transform 40 μl of competent E. coli DH5αF' cells and plated on 2YT plates (16 g Tryptone; 10 g Yeast extract; 10 g NaCl per liter $H_2O$) containing ampicillin, Xgal and IPTG. To verify pFBY23, whites colonies are picked after 16 h incubation at 37° C. and miniscreened using EcoRI HindIII double digest to confirm the presence of the correct insert and a HindIII/ BamHI double digest to show the BamHI linker in the previous FspI site.

EXAMPLE 20

Construction of pFBY24

2 μg of pFBY23 is cleaved to completion by HindIII and EcoRI in CA buffer. Theses fragment are separated on a 0.8% LGT gel in TAE buffer. The 701 bp band is cut out and the DNA is purified by ElutipD® chromatography.

2 μg of pFBY2 is cleaved to completion by HindIII and PstI in CA buffer. These fragments are separated on a 0.8% LGT gel in TAE buffer. The 3.8 kbp fragment is cut out and the DNA is purified by ElutipD® chromatography.

2 μg of pFBY2 is cleaved to completion by PstI and XbaI in CA buffer. These fragments are separated on a 0.8% LGT gel in TAE buffer. The 1.95 kbp fragment is cut out and the DNA is purified by ElutipD® chromatography.

2 μg of pFBY2 is cleaved to completion by XbaI and EcoRI in CA buffer. These fragments are separated on a 0.8% LGT gel in TAE buffer. The 2.9 kbp fragment is cut out and the DNA is purified by ElutipD® chromatography.

Approximately 20 ng of each of the prepared fragments are ligated together in the presence of 1 mM ATP and ligation buffer by 0.5 units of T4 ligase for 3 h at room temperature.

This ligation mixture is used to transform 40 μl of competent E. coli DH5αF' cells and plated on 2YT plates containing ampicillin, Xgal and IPTG. After 16 h incubation at 37° C., white colonies are picked and miniscreened using HindIII EcoRI and PstI XbaI double digests to confirm the presence of the correct inserts and BamHI to show the presence of the new BamHI site.

pFBY24 is identical to pFBY2 with the complete sequences of the plasmids pTZ18R and 2μ separated by directly repeated FRT sites, except for the insertion of a BamHI site into the FspI site at the 3' end of the FLP gene.

EXAMPLE 21

Construction of pFBY74

2 μg of pFBY29 is cleaved to completion by BamHI in CA buffer. These fragments are separated on a 0.8% LGT gel in TAE buffer. The 2.0 kbp band is cut out and the DNA is purified by ElutipD® chromatography.

2 μg of pFBY24 is cleaved to completion by BamHI in CA buffer. The 5' phosphate groups are removed with 500 units of BAP in BAP buffer (50 mM Tris(hydroxymethyl) aminomethane; 50 mM NaCl; HCl to pH 8.0) at 65° C. for 30 min to prevent self ligation of the vector. These fragments are separated on a 0.8% LGT gel in TAE buffer. The 9.3 kbp band is cut out and the DNA is purified by ElutipD® chromatography.

Approximately 20 ng of the prepared fragments are ligated together in the presence of 1 mM ATP and ligation buffer by 0.5 units of T4 ligase for 3 h at room temperature.

This ligation mixture is used to transform 40 μl of competent E. coli DH5αF' cells and plated on 2YT plates containing ampicillin, Xgal and IPTG. After 16 h incubation at 37° C., whites colonies are picked and miniscreened using BamHI and a SalI XbaI double digest to confirm the presence and orientation of the correct inserts. The LEU2 gene is in the same orientation as ampR of pFBY74.

pFBY74 is a symmetric LEU2 containing two-micron plasmid that loses the bacterial sequences in yeast.

EXAMPLE 22

Construction of plasmids pMK5×1 and pMK5×2: Two symmetric 2 micron plasmids that loose the bacterial sequences in yeast and contain the CUP1p-hirudin expression cassette 2 μg of plasmid pFBY4 are cleaved with EcoRI. The obtained DNA-fragment is run on a preparative 0.8% agarose gel, cut out and purified by ElutipD® chromatography (Schleicher und Schüll, Dassel, Germany). The fragment is subsequently blunt-ended with 1 unit T4 polymerase in the presence of 0.05 mM each of dATP, dCTP, dGTP and dTTP for 30 min at 37° C. The polymerase is heat-inactivated at 65° C. for 10 min.

Approximately 30 ng of fragment are ligated together with 0.4 pmoles of an unphosphorylated SalI linker of the sequence GGTCGACC and 1 mM ATP by 0.5 units of T4 ligase for 3 h at room temperature. The ligation mixture is used to transform competent E. coli DH5αF' cells (Hanahan, D.: J. Mol. Biol. 166 (1983), 557 and the cells are plated on LB medium plus ampicillin. Ampicillin resistant colonies are picked and analysed by cutting their plasmid DNA with SalI to show the SalI linker in the previous EcoRI site. The obtained plasmid is called pMK2.

2 μg of pMK2 are cut with BamHI. The 5' phosphate groups are removed with 500 units of BAP (bovine alkaline phosphatase) in BAP-buffer at 65° C. for 30 min. The fragment is run on a preparative 0.8% agarose gel, cut out and purified by ElutipD® chromatography (Schleicher und Schüll, Dassel, Germany). The fragment is subsequently blunt-ended with 1 unit T4 polymerase in the presence of 0.05 mM each of dATP, dCTP, dGTP and dTTP for 30 min at 37° C. The polymerase is heat-inactivated at 65° C. for 10 min.

2 μg of pPFY53 (see example 1) are cleaved with SalI. The 1.3 kb fragment containing the CUP1p-hirudin expression cassette is separated on a 0.8% agarose gel, purified and blunt-ended with T4 polymerase as described above. Approximately 20 ng of each of the prepared fragments are ligated together in the presence of 1 mM ATP by 0.5 units of T4 ligase for 3 h at room temperature. The ligation mixture is used to transform competent E. coli DH5αF' cells (Hanahan, D.: J. Mol. Biol. 166 (1983), 557) and the cells are plated on LB medium plus ampicillin. Ampicillin resistant colonies are picked and analysed using XbaI to confirm the presence of the correct insert and to determine the orientation. The generated plasmids are called pMK3/1 and pMK3/2. pMK3/1 contains the CUP1p-hirudin expression cassette in the same orientation as compared to the URA3 gene, whereas pMK3/2 contains the respective genes in the reverse orientation.

2 μg of pFBY74 are cut with SnaBI. The 5' phosphate groups are removed with BAP and the obtained DNA-fragment is purified via an 0.8% agarose gel and ElutipD® chromatography as described above. 2 μg of pMK3/2 are cut with SalI. The 2.6 kb fragment, containing the CUP1p-hirudin expression cassette and the URA3 gene is gel-purified and blunt-ended as described above. Approximately 20 ng of each, cut pFBY74 and the pMK3/2 fragment are ligated together and transformed into competent E. coli DH5αFα cells as described above. Ampicillin resistant colonies are analysed cutting their plasmid DNA with SalI and NcoI to confirm the correct insert and to determine the orientation. Two plasmids are obtained called pMK5×1 and pMK5×2. The difference between these two plasmids is that in the former the CUP1p-hirudin expression cassette has the reverse and the latter the same orientation as compared to the LEU2 gene.

EXAMPLE 23

Switching the mating type of strain TR1456

The generation of a diploid yeast strain normally occurs via mating of two haploid strains of the α and a mating type, resp. In order to obtain the isogenic diploid version of the haploid strain TR1456, mating type a (see Example 5), the opposite mating type of Tr1456 has to be engineered via mating type switching. Background and principle of this method are outlined in Herskowitz and Jensen (1991), Methods in Enzymology, Vol. 194, p. 132–146.

Strain TR1456 is transformed with plasmid pGAL-HO, which contains the HO endonuclease gene under control of the GAL10 promoter, the URA3 marker and CEN4 functions (Herskowitz and Jensen (1991), Methods in Enzymology, Vol. 194, p. 132–146). Transformation and selection on yeast minimal medium supplemented with leucine and deficient in uracil is performed as described in Example 5. Single transformed yeast clones are isolated and one clone is grown in 20 ml synthetic medium composed of (g/l):

| | |
|---|---|
| Difco yeast nitrogen base w/o amino acids | 8.4 |
| L-asparagine | 10 |
| L-histidine | 1 |
| L-leucine | 0.1 |
| glucose | 20 |

The preculture is grown overnight at 30° C. and 180 rpm. Subsequently the culture is diluted 20 times in the medium described above, but containing only 0.25% glucose. The culture is again incubated at 30° C. and 180 rpm and glucose consumption monitored using glucose tester sticks (Diabur-Test 500®, Boehringer Mannheim). As soon as the glucose is exhausted, galactose is added to the flask to a final concentration of 2% to induce the GAL10 promoter. After 7 h of incubation at 30° C. and 180 rpm 1 ml of the culture is withdrawn, and the cells washed and resuspended in 10 ml of the complex medium described in Example 7, and further incubated for 4 h at 30° C. and 180 rpm. Subsequently, a sample of the cells is withdrawn, diluted in distilled water and plated out at a concentration of approximately 200 cells per plate on the following complex medium (g/l):

| Bacto yeast extract | 20 |
|---|---|
| Bacto peptone | 10 |
| Bacto agar | 20 |
| glucose | 20 |

The plates are incubated at 30° C. for 2 days until the colonies reach a size of approximately 2 mm.

The colonies are then tested for cell type (a, α or a/α) by the standard assay for mating factor production ('halo assay'). The procedure used is described extensively by Sprague (1991), Methods in Enzymology, Vol. 194, p.77–93.

Eight colonies exhibiting the α-mating type are picked and each is inoculated into 5 ml of the following complex medium (g/l):

| Bacto peptone | 20 |
|---|---|
| Bacto yeast extract | 10 |
| glucose | 20 |

The cells are grown for 16 h at 30° C. and 180 rpm. A sample of cells is withdrawn, diluted in distilled water and plated out at a concentration of approximately 200 cells per plate on the complex medium described above. The plates are incubated at 30° C. for 2 days until the colonies reach a size of approximately 2 mm. These colonies are rechecked for the α-mating type using the 'halo-assay'. Concomitantly the colonies are replicaplated on minimal medium supplemented with leucine and deficient in uracil as described in Example 5. Colonies that have lost the pGAL-HO plasmid cannot grow on this medium, since they lack the URA3 marker.

One colony that repeatedly exhibits the α-mating type and has lost the pGAL-HO plasmid, is picked and restreaked on complex medium. The strain represents the isogenic, α-mating type counterpart of TR1456 and is called GPY11.

EXAMPLE 24

Diploid formation using strains TR1456a and GPY11α

Patches of strain TR1456 and strain GPY11 are carefully mixed with a toothpick on a YPD plate consisting of (g/l):

| Bacto peptone | 20 |
|---|---|
| Bacto yeast extract | 10 |
| glucose | 20 |
| Bacto agar | 10 |

The plate is incubated at room temperature to allow the cells to mate. After approximately 12 h an inoculum of the mating mixture is diluted with distilled water and an aliquot is applied to a YPD plate as a single steak. The plate is subjected to micromanipulation using a CIT Alcatel Micromanipulator in conjunction with a Leitz microscope (magnification 250 times). Zygotes are easily detectable microscopically by their characteristic shape. 10–20 potential zygotes are separated from the mating mixture on the YPD plate. The plate is then incubated at room temperature for 2–3 days until the zygotes have formed colonies. The diploid status of the zygotes is verified by performing the 'halo assay' for mating pheromone production as described above. Diploid cells do not secrete either α-factor or a-factor.

One verified diploid colony is chosen and called GPY18. It represents the isogenic diploid version of strain TR1456.

EXAMPLE 25

Desulphatohirudin production by strains TR1456 and GPY18 transformed with plasmid pPFY56 or pMK5x2 grown in shake flasks on complex medium Cells of strain TR1456 and GPY18 are transformed with plasmids pPFY56 (Example 1) and pMK5x2 (Example 22), resp., as described in Example 5.

Strains TR1456/pPFY56, TR1456/pMK5x2, GPY18/pPFY56 and GPY18/pMK5x2 are each grown in a preculture (10 ml; composition described in Example 23) for 72 h at 28° C. and 250 rpm. The medium of the main culture (50 ml) is described in Example 7, except that copper sulphate is added to a concentration of 1 mM. The main culture is inoculated with cells from the preculture at an OD 600 of 0.1. The cultures are grown up to 72 h at 28° C. and 250 rpm. After the fermentation the cells are removed by centrifugation and the amount of desulphatohirudin in the supernatant measured by HPLC as disclosed in EP-A-340 170. The results are summarized in table 8.

TABLE 8

| Strain/plasmid | Desulphatohirudin production (mg/l) fermentation time | | |
|---|---|---|---|
| | 24h | 48h | 72h |
| TR1456/pPFY56 | 47 | 131 | 245 |
| GPY18/pPFY56 | 64 | 158 | 277 |
| TR1456/pMK5x2 | 50 | 172 | 328 |
| GPY18/pMK5x2 | 67 | 194 | 348 |

Under the conditions of the experiment, the diploid strain GPY18 shows higher hirudin titers as compared to the haploid parent strain TR1456. Transformation with plasmid pMK5x2 leads to higher hirudin titers in either the haploid or the diploid strain as compared to plasmid pPFY56.

Deposition of microorganisms

The following microorganism strains were deposited at the Deutsche Sammlung yon Mikroorganismen (DSM), Mascheroder Weg 1b, D-3000 Braunschweig (accession numbers and deposition dates given):

| Saccharomyces cerevisiae H449 | DSM 4413 February 18, 1988 |
|---|---|
| Saccharomyces cerevisiae HT462/TH3 | DSM 7190 July 22, 1992 |
| E. coli DH5αF'/pFBY2 | DSM 6271 December 14, 1990 |
| E. coli DH5αF'/pFBY4 | DSM 6272 December 14, 1990 |
| E. coli DH5αF'/pFBY5 | DSM 6273 December 14, 1990 |
| E. coli DH5αF'/pFBY29 | DSM 6275 December 14, 1990 |
| E. coli JM109/pDP34 | DSM 4473 March 14, 1988 |

We claim:

1. A method for the production of desulphatohirudin comprising the steps of:
   culturing in a complex medium a yeast strain harboring a yeast expression vector comprising a desulphatohirudin expression cassette consisting of the yeast CUP1 promoter operably linked to a first DNA sequence encoding a yeast signal peptide, said first DNA sequence operably linked to a second DNA sequence encoding desulphatohirudin, and a third DNA sequence containing a yeast transcription termination signal, thereby secreting desulphatohirudin into the complex medium, and
   isolating the desulphatohirudin secreted into the complex medium, wherein the complex medium contains a CUP1 promoter-inducing amount of a copper salt throughout the entire culturing step.

2. The method according to claim 1, wherein the desulphatohirudin is selected from the group consisting of desulphatohirudin variants HV1, HV2, HV3, and derivatives of HV1, HV2, and HV3 which have thrombin inhibiting activity.

3. The method according to claim 1, wherein the desulphatohirudin is desulphatohirudin variant HV1.

4. The method according to claim 1, wherein the yeast strain is a strain of *Saccharomyces cerevisiae*.

5. The method according to claim 1, wherein the yeast strain is a cir° strain of *Saccharomyces cerevisiae*.

6. The method according to claim 1, wherein the yeast strain is single protease-deficient or multiple protease-deficient.

7. The method according to claim 6, wherein the yeast strain is deficient in carboxypeptidase yscα and yscY proteolytic activity.

8. The method according to claim 1, wherein the yeast strain contains 0–16 copies of the chromosomal CUP1 gene.

9. The method according to claim 1, wherein the yeast strain contains 2–4 copies of the ACE1 gene.

10. The method according to claim 1, wherein the yeast strain has a ploidy greater than or equal to two.

11. The method according to claim 10, wherein the yeast strain is diploid.

12. A yeast expression vector comprising a desulphatohirudin expression cassette consisting of the yeast CUP1 promoter operably linked to a first DNA sequence encoding a yeast signal peptide, said first DNA sequence operably linked to a second DNA sequence encoding desulphatohirudin, and a third DNA sequence containing a yeast transcription termination signal.

13. The yeast expression vector according to claim 12, wherein the CUP1 promoter comprises the nucleotide sequence set forth as SEQ ID NO:1.

14. The yeast expression vector according to claim 12, wherein the yeast signal peptide is selected from the group consisting of the signal peptides of yeast invertase, α-factor, pheromone peptidase, killer toxin and repressible acid phosphatase and the signal peptide of *Aspergillus awamori* glucoamylase.

15. The yeast expression vector according to claim 12, wherein the signal peptide is selected from the group consisting of the signal peptides of yeast invertase and repressible acid phosphatase.

16. The yeast expression vector according to claim 12, wherein the third DNA sequence is the 3' flanking sequence of a yeast gene, said 3' flanking sequence comprising a transcription termination signal sequence and a polyadenylation sequence.

17. The yeast expression vector according to claim 12, wherein the yeast expression vector comprises a two-micron plasmid.

18. The yeast expression vector according to claim 12, further comprising 1 to 3 additional said desulphatohirudin expression cassettes.

19. The yeast expression vector according to claim 12, further comprising an ACE1 expression cassette.

20. The yeast expression vector according to claim 12, wherein the yeast expression vector lacks a bacterial sequence.

21. A yeast strain harboring a yeast expression vector comprising a desulphatohirudin expression cassette consisting of the yeast CUP1 promoter operably linked to a first DNA sequence encoding a yeast signal peptide, said first DNA sequence operably linked to a second DNA sequence encoding desulphatohirudin, and a third DNA sequence containing a yeast transcription termination signal.

22. The yeast strain according to claim 21, wherein the yeast strain has a ploidy greater than or equal to two.

23. The yeast strain according to claim 22, wherein the yeast strain is diploid.

24. The method according to claim 1, wherein the yeast strain contains 2–6 copies of the chromosomal CUP1 gene.

* * * * *

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 1082 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..6
        ( D ) OTHER INFORMATION: /function="BamHI linker"

( i x ) FEATURE:
        ( A ) NAME/KEY: promoter
        ( B ) LOCATION: 7..432
        ( D ) OTHER INFORMATION: /standard_name= "CUP1 promoter"

( i x ) FEATURE:
        ( A ) NAME/KEY: misc_feature
        ( B ) LOCATION: 433..441
        ( D ) OTHER INFORMATION: /function="EcoRI linker"

( i x ) FEATURE:
        ( A ) NAME/KEY: sig_peptide
        ( B ) LOCATION: 442..492
        ( D ) OTHER INFORMATION: /standard_name= "PHO5 signal
            sequence"

( i x ) FEATURE:
        ( A ) NAME/KEY: mat_peptide
        ( B ) LOCATION: 493..690
        ( D ) OTHER INFORMATION: /product="Desulphatohirudin HV1"
            / standard_name= "HV1"

( i x ) FEATURE:
        ( A ) NAME/KEY: terminator
        ( B ) LOCATION: 691..1068
        ( D ) OTHER INFORMATION: /standard_name= "PHO5 transcription
            terminator"

( i x ) FEATURE:
        ( A ) NAME/KEY: misc_feature
        ( B ) LOCATION: 1069..1082
        ( D ) OTHER INFORMATION: /function="SalI linker"

( i x ) FEATURE:
        ( A ) NAME/KEY: CDS
        ( B ) LOCATION: 442..690
        ( D ) OTHER INFORMATION: /product="primary transcript"

( x i ) SEQUENCE DESCRIPTION: SEQ ID NO: 1:

```
GGATCCCCAT   TACCGACATT   TGGGCGCTAT   ACGTGCATAT   GTTCATGTAT   GTATCTGTAT         60

TTAAAACACT   TTTGTATTAT   TTTTCCTCAT   ATATGTGTAT   AGGTTTATAC   GGATGATTTA        120

ATTATTACTT   CACCACCCTT   TATTTCAGGC   TGATATCTTA   GCCTTGTTAC   TAGTTAGAAA        180

AAGACATTTT   TGCTGTCAGT   CACTGTCAAG   AGATTCTTTT   GCTGGCATTT   CTTCTAGAAG        240

CAAAAGAGC    GATGCGTCTT   TTCCGCTGAA   CCGTTCCAGC   AAAAAAGACT   ACCAACGCAA        300

TATGGATTGT   CAGAATCATA   TAAAAGAGAA   GCAAATAACT   CCTTGTCTTG   TATCAATTGC        360

ATTATAATAT   CTTCTTGTTA   GTGCAATATC   ATATAGAAGT   CATCGAAATA   GATATTAAGA        420

AAAACAAACT   GTGAATTCAA   A ATG TTT AAA TCT GTT GTT TAT TCA ATT TTA               471
                            Met Phe Lys Ser Val Val Tyr Ser Ile Leu
                            -17     -15             Val              -10
```

```
GCC GCT TCT TTG GCC AAT GCA GTT GTT TAC ACC GAC TGT ACC GAA TCT    519
Ala Ala Ser Leu Ala Asn Ala Val Val Tyr Thr Asp Cys Thr Glu Ser
         -5              1               5

GGT CAA AAC TTG TGT TTG TGT GAA GGT TCT AAC GTT TGT GGT CAA GGT    567
Gly Gln Asn Leu Cys Leu Cys Glu Gly Ser Asn Val Cys Gly Gln Gly
 10              15              20              25

AAC AAG TGT ATC TTG GGT TCT GAC GGT GAA AAG AAC CAA TGT GTT ACC    615
Asn Lys Cys Ile Leu Gly Ser Asp Gly Glu Lys Asn Gln Cys Val Thr
             30              35              40

GGT GAA GGT ACC CCA AAG CCA CAA TCT CAC AAC GAC GGT GAC TTC GAA    663
Gly Glu Gly Thr Pro Lys Pro Gln Ser His Asn Asp Gly Asp Phe Glu
         45              50              55

GAA ATC CCA GAA GAA TAC TTG CAA TAGGATCCTG GTACGTTCCT CAAGGTGCTC   717
Glu Ile Pro Glu Glu Tyr Leu Gln
         60              65

GTGTCTACAC CGAAAAATTC CAATGTTCTA ACGACACCTA CGTCAGATAC GTCATTAACG   777

ATGCTGTTGT TCCAATTGAA ACCTGTTCCA CTGGTCCAGG GTTCTCTTGT GAAATCAATG   837

ACTTCTACGA CTATGCTGAA AAGAGAGTAG CCGGTACTGA CTTCCTAAAG GTCTGTAACG   897

TCAGCAGCGT CAGTAACTCT ACTGAATTGA CCTTCTACTG GGACTGGAAC ACTACTCATT   957

ACAACGCCAG TCTATTGAGA CAATAGTTTT GTATAACTAA ATAATATTGG AAACTAAATA  1017

CGAATACCCA AATTTTTTAT CTAAATTTTG CCGAAAGATT AAAATCTGCA GCCAAGCTGG  1077

TCGAC                                                              1082
```

(2) INFORMATION FOR SEQ ID NO: 2:

(i) SEQUENCE CHARACTERISTICS:
        (A) LENGTH: 82 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Phe Lys Ser Val Val Tyr Ser Ile Leu Ala Ala Ser Leu Ala Asn
-17     -15                 -10                 -5

Ala Val Val Tyr Thr Asp Cys Thr Glu Ser Gly Gln Asn Leu Cys Leu
    1               5               10                      15

Cys Glu Gly Ser Asn Val Cys Gly Gln Gly Asn Lys Cys Ile Leu Gly
                20              25              30

Ser Asp Gly Glu Lys Asn Gln Cys Val Thr Gly Glu Gly Thr Pro Lys
            35              40                      45

Pro Gln Ser His Asn Asp Gly Asp Phe Glu Glu Ile Pro Glu Glu Tyr
        50              55              60

Leu Gln
    65
```

(2) INFORMATION FOR SEQ ID NO: 3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..28
        (D) OTHER INFORMATION: /product="PCR primer"

( x i ) SEQUENCE DESCRIPTION: SEQ ID NO: 3:

GGATCCATTA CCGACATTTG GGCGCTAT 28

( 2 ) INFORMATION FOR SEQ ID NO: 4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..30
        ( D ) OTHER INFORMATION: /product="PCR primer"

( x i ) SEQUENCE DESCRIPTION: SEQ ID NO: 4:

GAATTCACAG TTTGTTTTTC TTAATATCTA 30

( 2 ) INFORMATION FOR SEQ ID NO: 5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..27
        ( D ) OTHER INFORMATION: /product="PCR primer"

( x i ) SEQUENCE DESCRIPTION: SEQ ID NO: 5:

GATATCGATC GTGAAAGAAT ATTTGCT 27

( 2 ) INFORMATION FOR SEQ ID NO: 6:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..29
        ( D ) OTHER INFORMATION: /product="PCR primer"

( x i ) SEQUENCE DESCRIPTION: SEQ ID NO: 6:

GATATCATGA GGATGATGAC AAAGAAGAC 29

( 2 ) INFORMATION FOR SEQ ID NO: 7:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..26
        ( D ) OTHER INFORMATION: /product="PCR primer"

( x i ) SEQUENCE DESCRIPTION: SEQ ID NO: 7:

```
CTGATAATCA GTGAATTCAC AGAATG                                    2 6
```